US010426552B2

(12) United States Patent
Davies et al.

(10) Patent No.: US 10,426,552 B2
(45) Date of Patent: Oct. 1, 2019

(54) REDUCTION METHODS FOR ALIGNING BONE SEGMENTS USING CUSTOMIZED JIGS

(71) Applicants: John Adam Davies, San Jose, CA (US); Albert Charles Lynch, Saratoga, CA (US)

(72) Inventors: John Adam Davies, San Jose, CA (US); Albert Charles Lynch, Saratoga, CA (US)

( * ) Notice: Subject to any disclaimer, the term of this patent is extended or adjusted under 35 U.S.C. 154(b) by 0 days.

(21) Appl. No.: 15/937,842

(22) Filed: Mar. 27, 2018

(65) Prior Publication Data

US 2018/0280090 A1   Oct. 4, 2018

Related U.S. Application Data

(60) Provisional application No. 62/477,931, filed on Mar. 28, 2017, provisional application No. 62/549,396, filed on Aug. 23, 2017.

(51) Int. Cl.
| | |
|---|---|
| *G06K 9/00* | (2006.01) |
| *A61B 34/10* | (2016.01) |
| *A61F 2/30* | (2006.01) |
| *G06K 9/32* | (2006.01) |
| *G06K 9/46* | (2006.01) |

(52) U.S. Cl.
CPC .......... *A61B 34/10* (2016.02); *A61F 2/30942* (2013.01); *G06K 9/00208* (2013.01); *A61B 2034/102* (2016.02); *A61F 2002/30948* (2013.01); *G06K 9/00671* (2013.01); *G06K 9/32* (2013.01); *G06K 9/4609* (2013.01); *G06K 2209/055* (2013.01)

(58) Field of Classification Search
None
See application file for complete search history.

(56) References Cited

U.S. PATENT DOCUMENTS

| | | | |
|---|---|---|---|
| 8,311,306 B2 | 11/2012 | Pavlovskaia | |
| 8,801,720 B2 | 8/2014 | Park | |
| 9,020,788 B2 | 4/2015 | Lang | |
| 2014/0324205 A1 | 10/2014 | Park | |
| 2015/0328004 A1 | 11/2015 | Mafhouz | |
| 2017/0249440 A1 | 8/2017 | Lang | |
| 2018/0049906 A1* | 2/2018 | Janzing | ..................... A61F 5/01 |
| 2018/0360609 A1* | 12/2018 | Steines | ..................... A61F 2/30 |

FOREIGN PATENT DOCUMENTS

WO       2012112694 A3      1/2013

OTHER PUBLICATIONS

F. Qiao, et al. Application of 3D Printed Customized External Fixator in Fracture Reduction, Injury (2015), Available at: http://dx.doi.org/10.1016/j.injury.2015.01.020.

* cited by examiner

*Primary Examiner* — Atiba O Fitzpatrick
(74) *Attorney, Agent, or Firm* — Daylight Law, P.C.

(57) ABSTRACT

Methods for aligning bone segments using custom jigs are disclosed. In one technique, bone segments are aligned using interaction elements, imaging, virtual fracture alignment, and a custom jig. The custom jig can be generated using a rapid fabrication method such as via the use of a three-dimensional printer. The methods can be minimally invasive or noninvasive. The interaction elements can be percutaneous interaction pins or noninvasive interaction elements.

24 Claims, 17 Drawing Sheets

FIG. 1
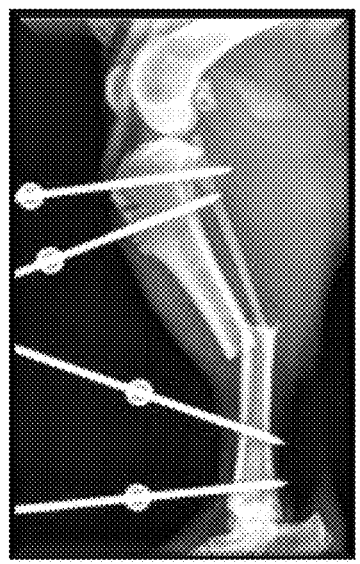
100
110
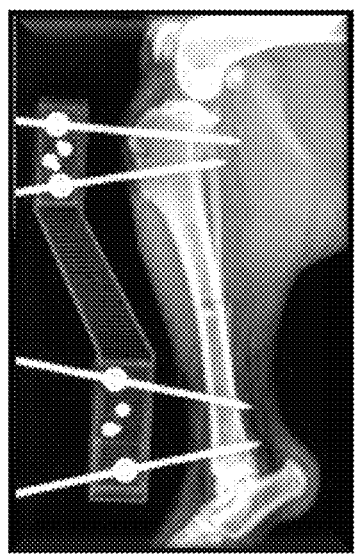
120
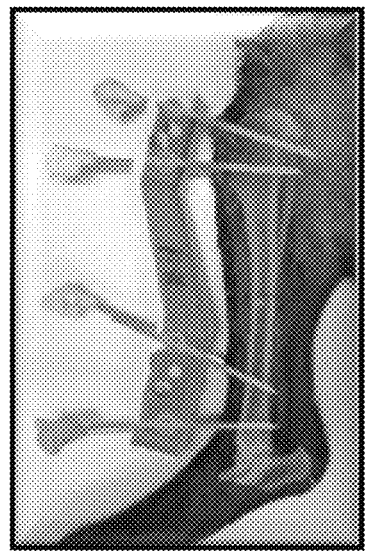
130

1300

FIG. 14
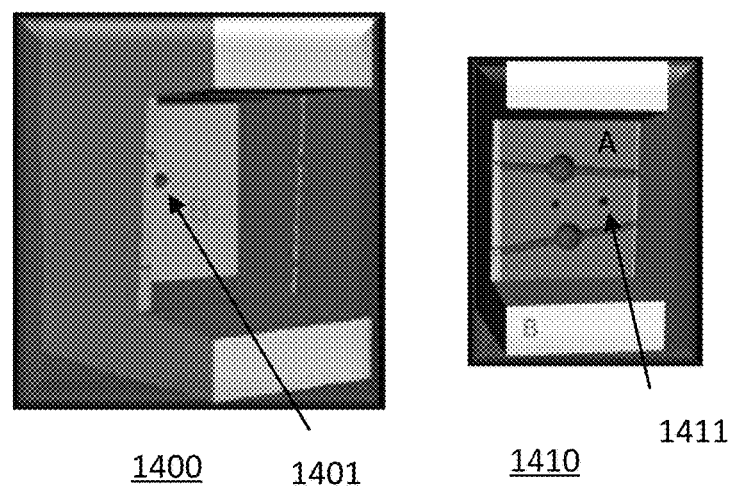
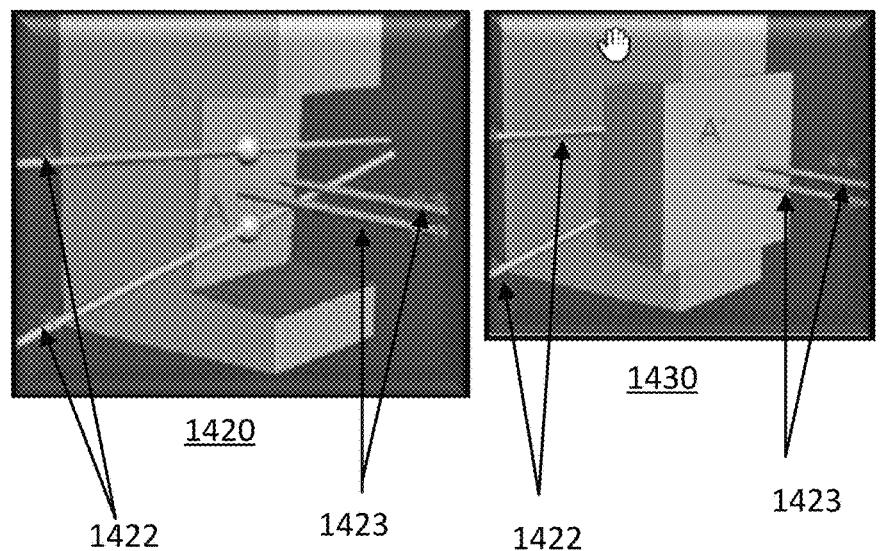

REDUCTION METHODS FOR ALIGNING BONE SEGMENTS USING CUSTOMIZED JIGS

CROSS REFERENCE TO RELATED APPLICATIONS

This application claims the benefit of U.S. Provisional Patent Application No. 62/477,931, filed Mar. 28, 2017, and U.S. Provisional Patent Application No. 62/549,396, filed Aug. 23, 2017, both of which are incorporated by reference herein in their entirety for all purposes.

BACKGROUND

Free bone segments require both stability and appropriate apposition of the segments as well as good blood supply to heal. Due to the high energy typically involved in bone fractures, highly fragmented fractures are commonly encountered. This amalgam of traumatized soft tissue and complex fracture morphology is effectively non-reconstructable within a reasonable timeframe typically associated with surgery. Further, the additional trauma to the blood supply and soft tissues incurred during an open surgical approach is detrimental to the local healing environment. This can result in malunions, non-unions, delayed healing, infections and suboptimal outcomes. In short, open surgical approaches are often not desirable. However, fractures frequently require some form of surgical intervention. The surgical intervention will generally involve reduction of the bone segments, which involves translating them into alignment. The reduction can be either open or closed. In open reduction, the fracture segments are exposed surgically by dissecting the surrounding tissues. In closed reduction, the manipulation of the bone segments is conducted in a minimally invasive manner and without full surgical exposure.

One surgical approach to bone reduction and stabilization is open reduction with internal fixation (ORIF). ORIF requires an open surgical approach to the fracture for anatomic reduction and rigid stabilization of all major fracture fragments. The size of the required incision in ORIF procedures can be large. This open approach damages the local blood supply along with the fracture hematoma and its beneficial cytokines. As a result, investigation into less invasive techniques that promote the use of the bodies' innate biological healing mechanisms and minimize disturbances to the local fracture biology have been gaining support.

Another surgical approach to bone reduction and stabilization is minimally invasive osteosynthesis (MIO). MIO places emphasis on preservation of the fracture biology, striving to maintain the local blood supply and fracture hematoma with its beneficial cytokines while restoring the bone to pre-fracture length and alignment. The applied minimally invasive definitive fixation then provides sufficient mechanical stability such that secondary bone healing via callus formation and osseous remodeling occurs, rather than the primary bone healing achieved with ORIF. Benefits of the MIO approach include reduced risk of post-operative infection, preservation of osteogenic potential and blood supply and faster healing.

Current techniques for MIO consist of external skeletal fixation (ESF), a hybrid open-but-do-not-touch (OBDNT) technique where the fracture site is opened but minimally disturbed, minimally invasive plate osteosynthesis (MIPO) and interlocking nail application. In all techniques where the fracture site is not exposed, the fracture site is manipulated via remote incisions, and reduction and definitive stabilization are assessed using intraoperative fluoroscopy during active surgical reduction. These techniques require intraoperative radiation exposure to operating room personnel and the patient, and are expensive.

SUMMARY

Methods and systems for aligning bone segments in a minimally or non-invasive manner are disclosed herein. The methods and systems can involve the use of customized jigs to reduce the bone segments by guiding interaction elements attached to the bone segments. The jigs can be reduction jigs. The interaction elements can be interaction pins or implants surgically attached to the bone segments, or elements located on an external sleeve or other supporting element that is attached to the bone segment indirectly and in a non-invasive manner. The customized jigs can be fabricated using a three-dimensional printer or any rapid hardware prototyping tool. The design for the customized jigs can be solved for via the virtual reduction of the bone segments using a model of the bone segments.

Various approaches for obtaining the model, conducting the virtual reduction, and generating the customized jig are described in the detailed description below. These approaches can include the use of computer tomography (CT) imaging to obtain a model of the bone segments, computer modeling in software to virtual reduce the bone segments, and three-dimensional printing to create a customized reduction jig. These approaches can attain and maintain bone alignment prior to definitive fixation in a sufficiently strong, efficient, and cost-effective manner. In certain approaches, the entire process of analyzing the bone segments, generating the jig, and physically reducing the bone segments using the jig can be conducted intraoperatively during a single operation and during a single session of anesthetics. Alternatively, as will be apparent from the following detailed disclosure, other approaches in accordance with this disclosure avoid the need for intraoperative imaging in that the analysis used to construct the jig can be conducted separately from the application of the jig and physical reduction of the bone segments in the operating room.

FIG. 1 provides four photographs of a specific application of the techniques disclosed herein in which a cadaveric canine tibial diaphyseal fracture is reduced to alignment in a minimally invasive manner. Image 100 provides an x-ray image of the fracture after interaction elements have been attached to the bone segments. In this specific approach, the interaction elements are interaction pins that have been surgically attached to the bone segments and that fully pierce the medullary cavity. Image 110 is a subsequent photograph of the cadaveric appendage with a custom jig attached to the interaction pins. Image 120 provides a subsequent x-ray image of the fracture, but after the interaction pins have been guided to reduction stops on the custom jig. As seen from image 120, the bone segments have been reduced to proper alignment using the custom jig and interaction pins. Image 130 is a modified photograph of the cadaveric appendage and custom jig that has been overlain with an x-ray image of both elements to show how reduction has been conducted without the need to dissect the tissue surrounding the bone segments.

A first reduction method for aligning a first bone segment and a second bone segment that is in accordance with some of the approaches in this disclosure includes the following steps. The method includes surgically attaching a first interaction implant to the first bone segment, and a second interaction implant to the second bone segment. The method also includes imaging the first and second bone segments to create a model. The method also includes processing the model to find an optimal bone alignment. The method also includes generating, based on the optimal bone alignment and with a three-dimensional printer, a custom jig. The custom jig includes a global jig element, a first local jig element, and a second local jig element. The method also includes attaching the first local jig element to the first interaction implant and attaching the second local jig element to the second interaction implants. The method also includes engaging, after attaching the custom jig to the first and second interaction implants, the first and second local jig elements with the global jig element. The first and second bone segments are translated as the first and second local jig elements are engaged with the global jig element. The first bone segment and second bone segment are properly aligned in the optimal bone alignment.

A second reduction method for aligning a first bone segment and a second bone segment that is in accordance with some of the approaches in this disclosure includes the following steps. The method includes attaching a first interaction implant to the first bone segment, and a second interaction implant to the second bone segment. The method also includes imaging the first and second bone segments to create a model. The method also includes processing the model to find an optimal bone alignment. The first bone segment and second bone segment are properly aligned in the optimal bone alignment. The method also includes generating, based on the optimal bone alignment and with a three-dimensional printer, a custom jig. The custom jig includes a global jig element and at least one local jig element. The method also includes attaching the custom jig to the first and second interaction implants. The method also includes engaging, after attaching the custom jig to the first and second interaction implants, the at least one local jig element with the global jig element. At least one of the first and second bone segments are translated as the at least one local jig element is engaged with the global jig element.

A third reduction method for aligning a first bone segment and a second bone segment that is in accordance with some of the approaches in this disclosure includes the following steps. The method includes attaching a first interaction element to the first bone segment and a second interaction element to the second bone segment. The method also includes imaging the first and second bone segments to create a model. The method also includes processing the model to find an optimal bone alignment. The first bone segment and second bone segment are aligned in the optimal bone alignment. The method also includes generating, with a three-dimensional printer, a custom jig. The method also includes guiding the first and second interaction elements with the custom jig. The first and second bone segments are aligned according to the optimal bone alignment when the first and second interaction elements are guided to a reduction stop on the custom jig.

BRIEF DESCRIPTION OF THE DRAWINGS

FIG. 1 provides four photographs of a specific application of custom jigs for bone segment reduction in accordance with some of the approaches disclosed herein.

FIG. 14 provides four views of the details of a local jig being engaged with a recess on a global jig in accordance with some of the approaches disclosed herein.

DETAILED DESCRIPTION

Specific methods and systems in accordance with the summary above are provided in this section. The methods and systems disclosed in this section are nonlimiting embodiments of the invention, and are provided for explanatory purposes only. The detailed disclosure of these specific embodiments should not be understood to constrict the full scope of the invention.

Figure 2:
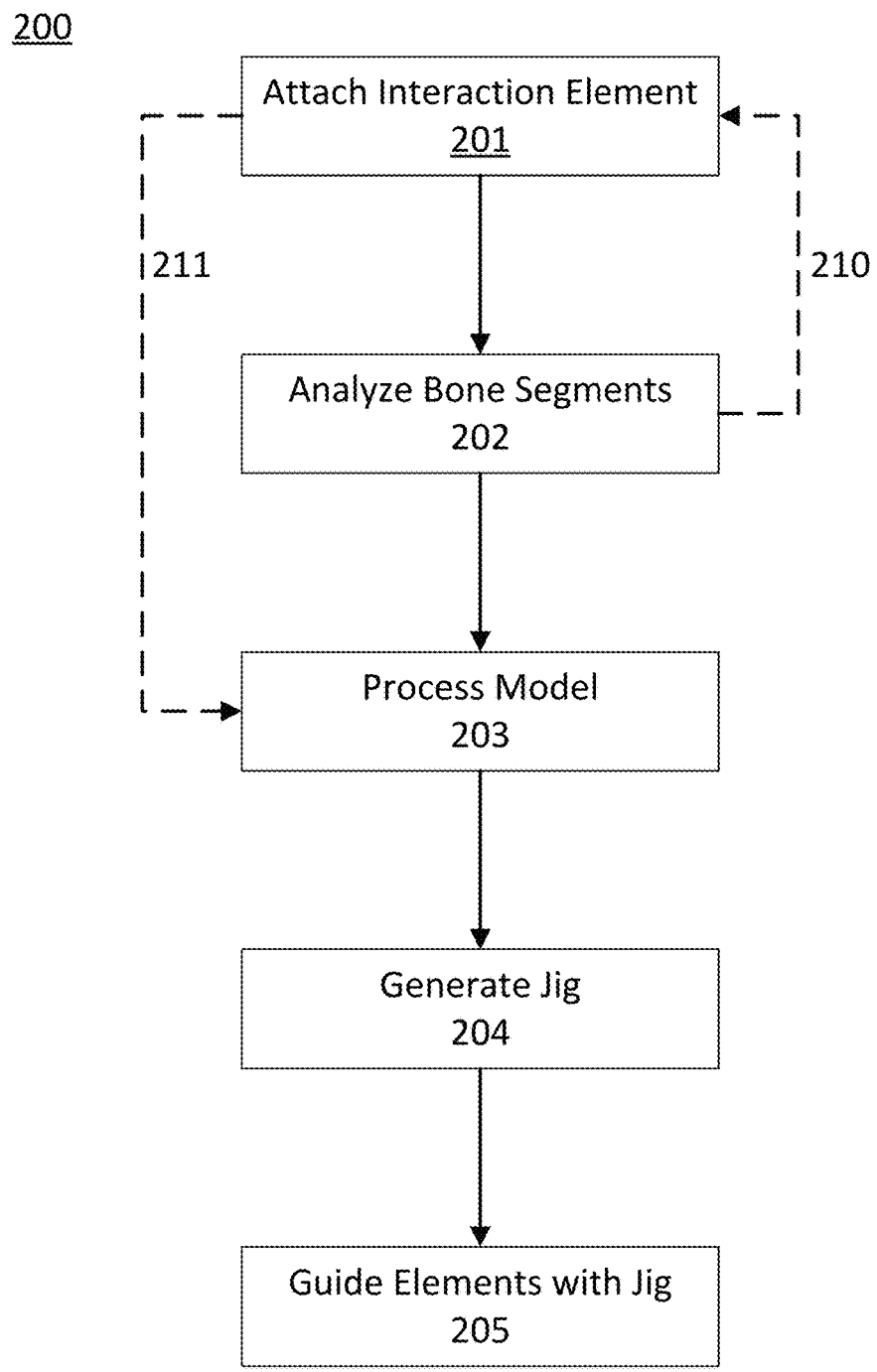
FIG. 2 provides a flow chart for a set of reduction methods for aligning bone segments that are in accordance with some of the approaches disclosed herein.

FIG. 2 provides a flow chart 200 for a set of reduction methods for aligning bone segments that are in accordance with some of the approaches disclosed herein. Flow chart 200 begins with either step 201, in which interaction elements are attached to the bone segments that will be reduced to alignment, or step 202, in which the bone segments are analyzed. Phantom connections 210 and 211 are provided to illustrate one of these alternatives in which the bone segments are analyzed first followed by attaching the interaction elements. Step 202 can involve imaging the bone segments using various imaging procedures such as fluoroscopy, CT imaging, magnetic resonance imaging (MRI) and other forms of imaging. Step 202 can include analyzing the bone segments using other methods of analysis that can be used to generate a digital model of the bone segments. In certain applications, the result of step 202 will be the generation of a digital model of the bone segments, with the interaction elements optionally included in that digital model, stored in a computer memory for processing in later steps of flow chart 200. Step 201 can involve surgically attaching percutaneous interaction elements to the bone segments or indirectly attaching interaction elements to the bone segments using the application of a topical interaction element such as a hard-shell sleeve or cuff placed around the bone segment. In approaches in which the bone segments are analyzed first, before the interaction elements are attached, connection 211 can involve an additional analysis of the interaction elements, or the addition of a virtual model of the interaction elements to the model. As disclosed below, step 202 can also be repeated twice. The step can be conducted to first determine which type of interaction element and reduction procedure is appropriate, and then be conducted a second time once those interaction elements have been attached. A description of this analysis is provided below with reference to FIG. 15.

Step 203 can involve processing the model to conduct a virtual reduction of the bone segments and solve for an optimal alignment. The optimal alignment may be stored in memory as positioning data for the bone segments, and optionally any included interaction elements. This step may involve the introduction of bone implants in order to reduce the bones in the face of missing bones mass. Various approaches for conducting this virtual reduction are discussed in more detail below. The approaches include fully automated processes conducted solely in software, manually reduction processes using the model and model manipulation software, and hybrid approaches that allow a user to provide a check on an automated reduction processes or that use automate techniques to facilitate a manual manipulation of the model by a user.

Step 204 can involve the generation of a custom jig using data obtained from the virtual reduction and the model of the bone segments. The custom jig can be configured to guide the interaction elements from a starting point to a reduction stop at which point the bone segments will be in the optimal alignment. The custom jig can be configured to guide the bone segments, via the interaction elements, along a translation path set by the virtual reduction. In step 205, the interaction elements are guided via the custom jig. The interaction elements can be guided from a start point to a reduction stop. Various approaches for conducting the attachment and analysis are discussed below. Various implementations of the interaction elements are discussed below with reference to the various kinds of customized jigs that can be used in accordance with the approaches disclosed herein.

The bone segments can be analyzed using method of analysis that lead to the generation of a digital model of the bone segments. As stated, the analysis can be conducted prior to attachment of any interaction elements, after attachment of interaction elements, or both before and after depending upon the application. The analysis can involve the use of high quality imaging via fluoroscopy, MRI, or CT imaging. Advanced imaging data of the damaged bone, with or without attached interaction elements, can then be stored in a standard industry format for analysis and manipulation such as the Digital Imaging and Communications in Medicine (DICOM) format.

The collected data can then be processed by software to generate a three-dimensional model of the bone segments. The software can include one or more modules that can be installed on the same system or different computer systems. The software can directly import both DICOM and non-DICOM data from an imaging center, picture archiving and communication system (PACS), or an external storage device. The software can utilize algorithms to reduce artifacts created during data acquisition. Both basic and advanced post-processing techniques are available (measuring, ROI, multiplanar (MPR) etc.), as well as application of stored templates to two dimensional and three-dimensional modified images.

The process of analyzing the bone segments can involve the software identifying the bone and allowing a user to confirm that identification. The process of analyzing the bone segments can also involve the software identifying the interaction elements, if present, and allowing a user to confirm that identification. The process can also involve segmenting the bone segments from any interaction elements in data for purposes of further analysis. However, as will be described below, the interaction elements and bone segments do not need to be treated as separate elements in all approaches before the three-dimensional model is generated. Landmarks for the bone segments, for example landmarks for a proximal fragment and distal articular fragment, can also be identified by the software and the user can be allowed the opportunity to confirm that identification. Landmarks can be selected until the fragment position in a three-dimensional space can be defined and stored as a three-dimensional model of the bone segments. The location of key mechanical stops and vectors for the interaction elements can also be identified in the same three-dimensional space and stored with the model of the bone segments.

Figure 3:
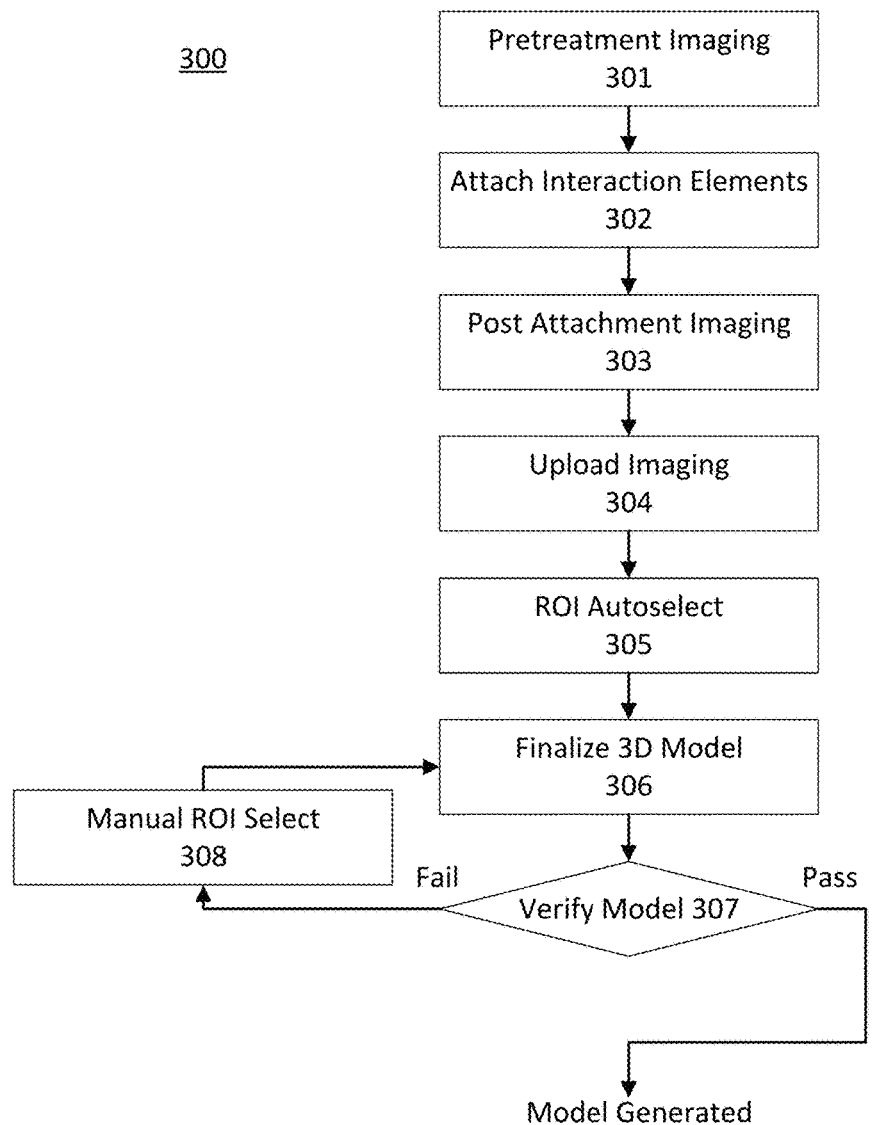
FIG. 3 provides a flow chart for a set of methods for generating a three-dimensional model of a set of bone segments, and optionally attached interaction elements, that are in accordance with some of the approaches disclosed herein.

FIG. 3 provides a flow chart 300 for a set of methods for generating a three-dimensional model of the bone segments, and optional interaction elements. In flow chart 300, the bone segments are analyzed, and the model of the bone segments is generated, using imaging. Flow chart 300 beings with pretreatment imaging 301. As stated, pretreatment imaging can be conducted to determine what kind of interaction elements, and what overall reduction procedure, will be required so that the procedure can be prepared prior to the patient being prepared for surgery. Detailed imaging is first performed on the bone in question to both describe the nature of the deformity and guide placement of interaction implants. The interaction implants can be selected from a suite of preconfigured shapes and sizes, or can be three-dimensionally printed or otherwise manufactured as a function of software modeling.

Flow chart 300 continues with a step 302 in which the interaction elements are attached to the bone segments. Flow chart 300 continues with post attachment imaging 303 in which the bone segments, along with the interaction elements, are imaged. This second set of imaging data can be used to generate the model of the bone segments. In this approach, the interaction elements are imaged along with the bone segments and will therefore be included in the generated model. In certain approaches, step 303 is optional. In particular, the step of pretreatment imaging 301 can be involve a procedure in which prefabricated drill guides are used to create pilot holes in the bone segments for future physical interaction implant placement. Imaging can be used to guide the creation of the pilot holes. Furthermore, imaging, or other analysis, can be used to capture the pilot holes for inclusion in the model of the bone segments. The virtual alignment process described herein can therefore, in these approaches, include the introduction of virtual interaction elements into the modeled pilot holes. Using this approach, the customizable jig for a given patient could be generated before the interaction elements were physically attached to the patient. As a result, the interaction elements could be surgically attached, using the aforementioned pilot holes, during the same operation used to conduct the physical reduction of the bone segments. For the avoidance of doubt, it is noted that in approaches in which only one round of imaging is utilized, those images will serve as the basis for generating the model. The imaging can then be uploaded and stored in a standard format in a step 304. For example, the imaging could be stored in DICOM format.

Figure 4:
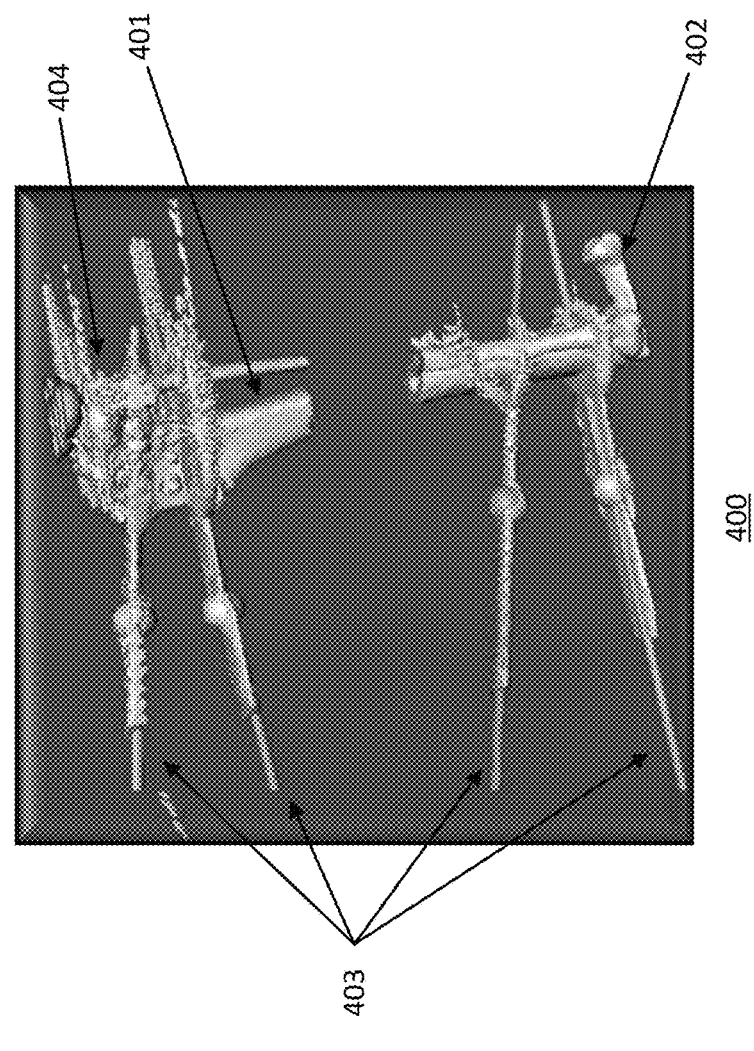
FIG. 4 provides an image of a pair of bone segments and attached interaction elements that can be used to generate a three-dimensional model in accordance with some of the approaches disclosed herein.

FIG. 4 provides an image 400 of two bone segments, 401 and 402, to provide an example of bone segments that have been imaged with interaction elements attached. In image 400 interaction elements in the form of interaction implants 403 have been surgically attached to bone segments 401 and 402. As seen in image 400, the implants themselves can cause significant distortion 404 in the image. This distortion is caused by flare magnification in situations where the interaction elements are metal. Techniques for eliminating the effect of this distortion on the accuracy of the reduction are discussed below. However, from image 400 itself it should be noted that the effect of this distortion can be mitigated by locating the attachment points of the interaction elements distant from the fracture. In certain approaches, additional processing may be required if interaction elements are attached prior to the generation of the model because the distortion could obscure landmarks that would otherwise be available for the generation of a three-dimensional model of the bone segments.

Returning to FIG. 3, the imaging uploaded in step 304 can be converted to a three-dimensional model via the identification of regions of interest (ROIs) and extrapolation using those ROIs. In steps 305 and 306, software automatically selects ROIs from the imaging and finalizes a three-dimensional model of the bone segments, and the optionally attached interaction elements. In step 307, the model can be verified by a user or via an automated process. If the model is verified, it is available for virtual reduction according to the methods described below. If the model is not verified, the flow chart can transition to step 308 in which a user is provided with the ability to manually select ROIs in the imaging. After this step is conducted, the software can again attempt to finalize a three-dimensional model of the bone segments. These steps can be repeated in a loop until the model is finalized. The three-dimensional model can be stored in a format compatible with three-dimensional modeling and printing.

Figure 5:
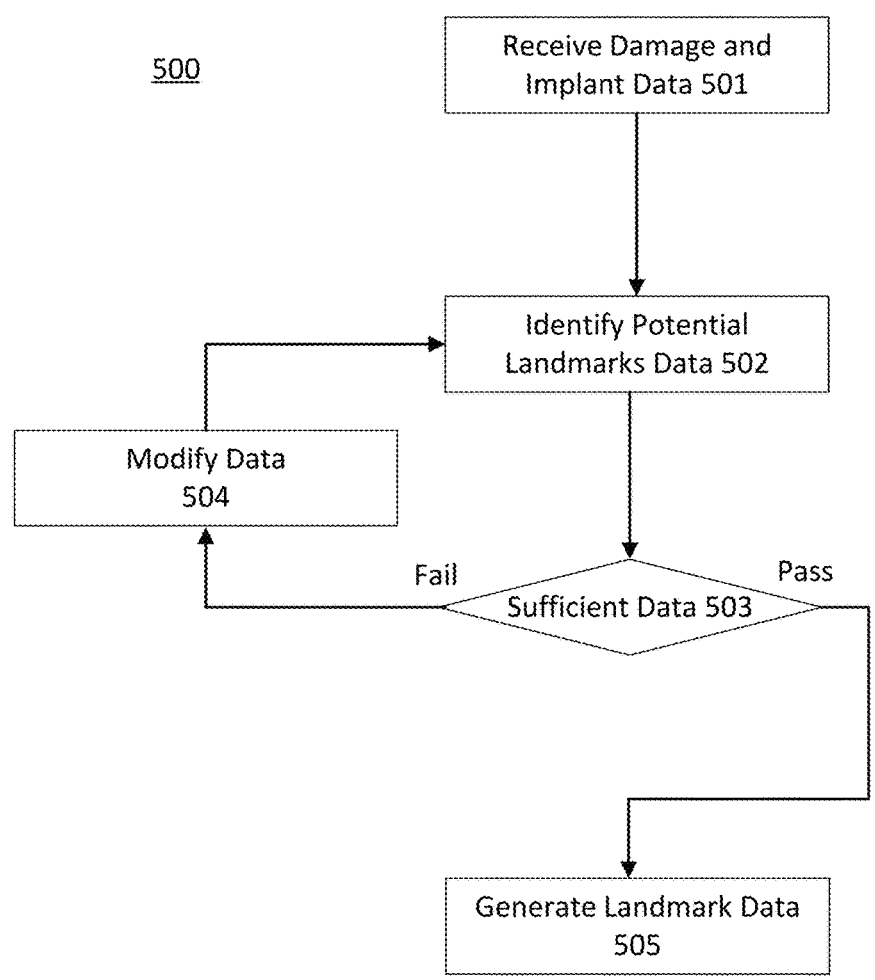
FIG. 5 provides a flow chart for a set of methods for generating landmark data to aide the generation of a three-dimensional model of a set of bone segments in accordance with some of the approaches disclosed herein.
Figure 6:
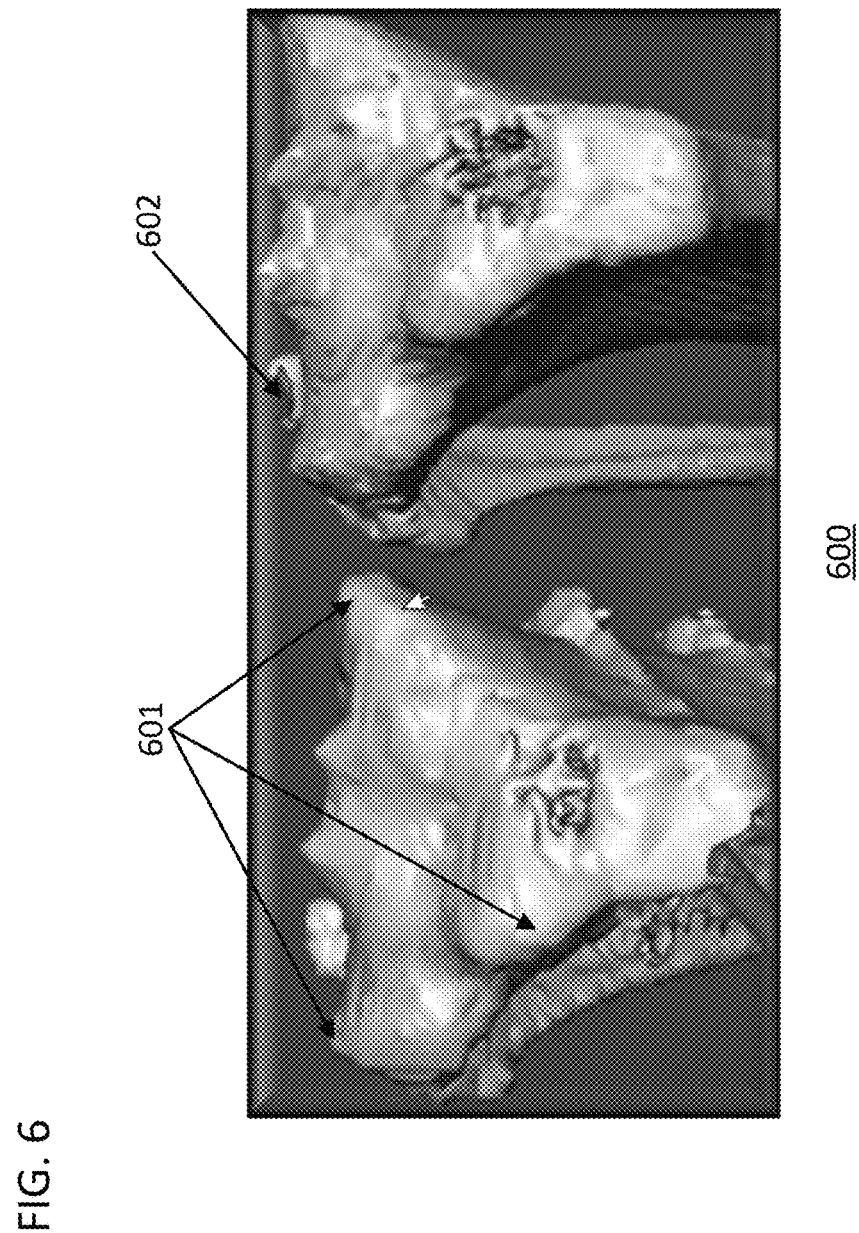
FIG. 6 provides an image of two bone segments to illustrate the selection of landmark data and removal of imaging artifacts in accordance with some of the approaches disclosed herein.

FIG. 5 illustrates a flow chart 500 for a set of methods that can be utilized to generate ROI data for use in flow chart 400 and similar approaches. In this specific example, bone segment landmarks are used as the ROIs for generating the model. Flow chart 500 beings with a step 501 of receiving damage and implant data 501. The damage and implant data can include imaging of the bone segments and interaction elements obtained when imaging the patient. FIG. 6 provides an image 600 of an example of the data that can be received in step 501.

Flow chart 500 continues with a step 502 of identifying potential landmark data for generating a three-dimensional model of the bone segments. The landmarks can be areas of the bone segments such as 601 in FIG. 6 which can be used to generate a three-dimensional model given common image processing techniques and a preprogrammed knowledge of bone morphology and anatomy generally. Flow chart 500 continues with a step 503 of checking to see if the number of landmarks is sufficient to generate a three-dimensional model. If this check fails, the flow chart proceeds to a step 504 in which the data is modified. Step 504 can involve the manual selection of additional landmarks by a user and identification of those landmarks to the software using a user interface. Step 504 can also involve manual editing of the imaging data to remove distortions that are easily identified by a user, such as distortion 602. The distortions can be removed by editing the image data or by selecting an alternative image in the imaging data in which the distortion is not present to be used for detecting landmarks. If the check conducted in step 503 passes, the landmark data can be generated in a step 505 and made available to a software module responsible for generating a three-dimensional model of the bone segments.

After analysis has been conducted on the bone segments to generate a three-dimensional model thereof, the bone segments can undergo a virtual reduction using any number of different techniques. The techniques can be fully automated or involve user input. When attempting to reconstruct a misaligned bone in three-dimensional space it can be difficult to align and translate the fragments into the desired location due to the complexity of the surface morphology and the inherent difficulty of manipulating a three-dimensional object through a two-dimensional visualization environment. As such, the process can be conducted using an augmented reality interface or three-dimensional display in which the user can manipulate the three-dimensional model in a true representation of the model's dimensionality. Also, various image processing techniques as described below can be used to manipulate the model for a virtual reduction. Regardless of the process used, the output of the virtual reduction can include an optimal alignment, optimal fit, given desired bone structure, areas of deficiency of prepared implants, and optimal orientation of the bone and any included interaction elements following reconstruction. In specific approaches, the output of the virtual alignment will be a predetermined spatial arrangement of bone segments and associated spatial arrangement of interaction elements. Any and all of this output data can be used to generate a customized jig in order to physically implement the virtual reduction.

Figure 7:
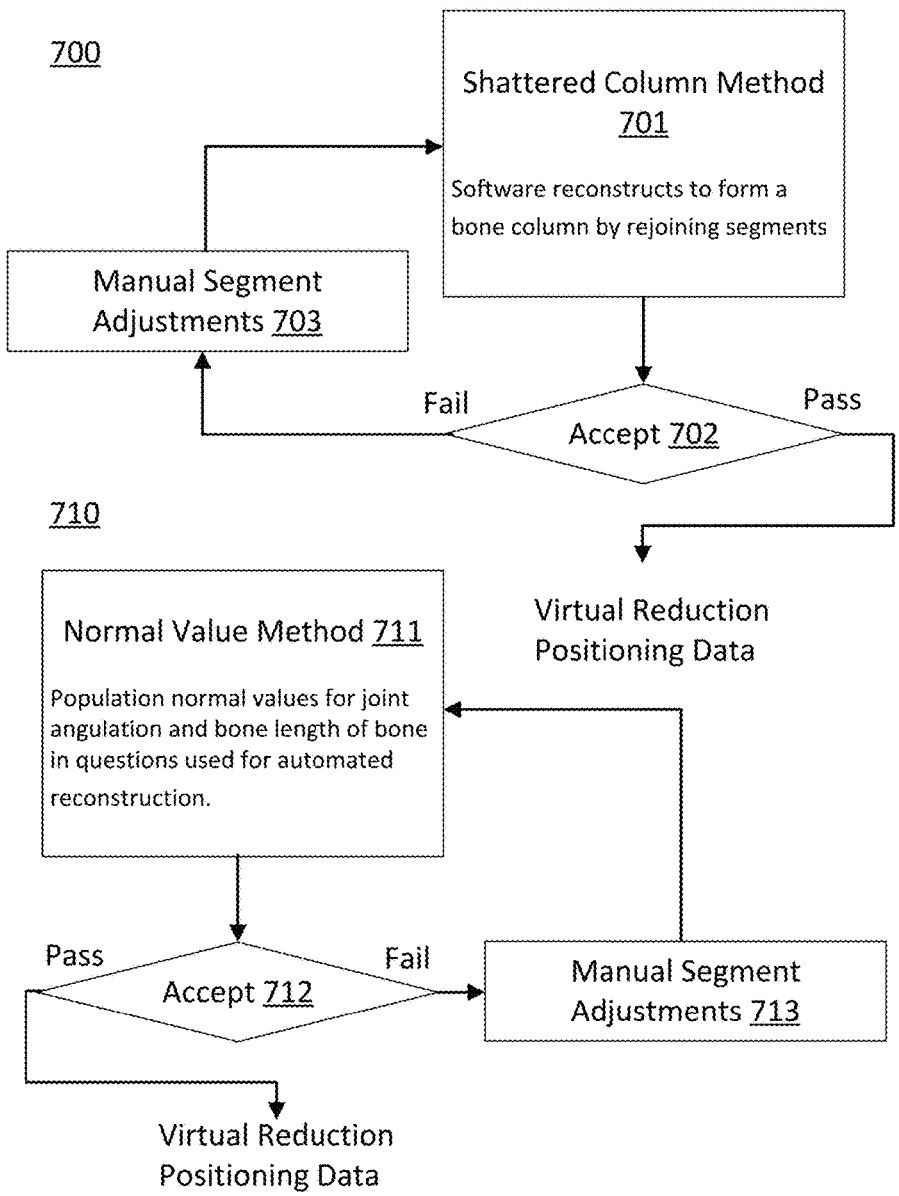
FIG. 7 provides two flow charts each for a set of methods for conducting a virtual reduction and generating an optimal bone alignment and virtual reduction positioning data in accordance with some of the approaches disclosed herein.
Figure 8:
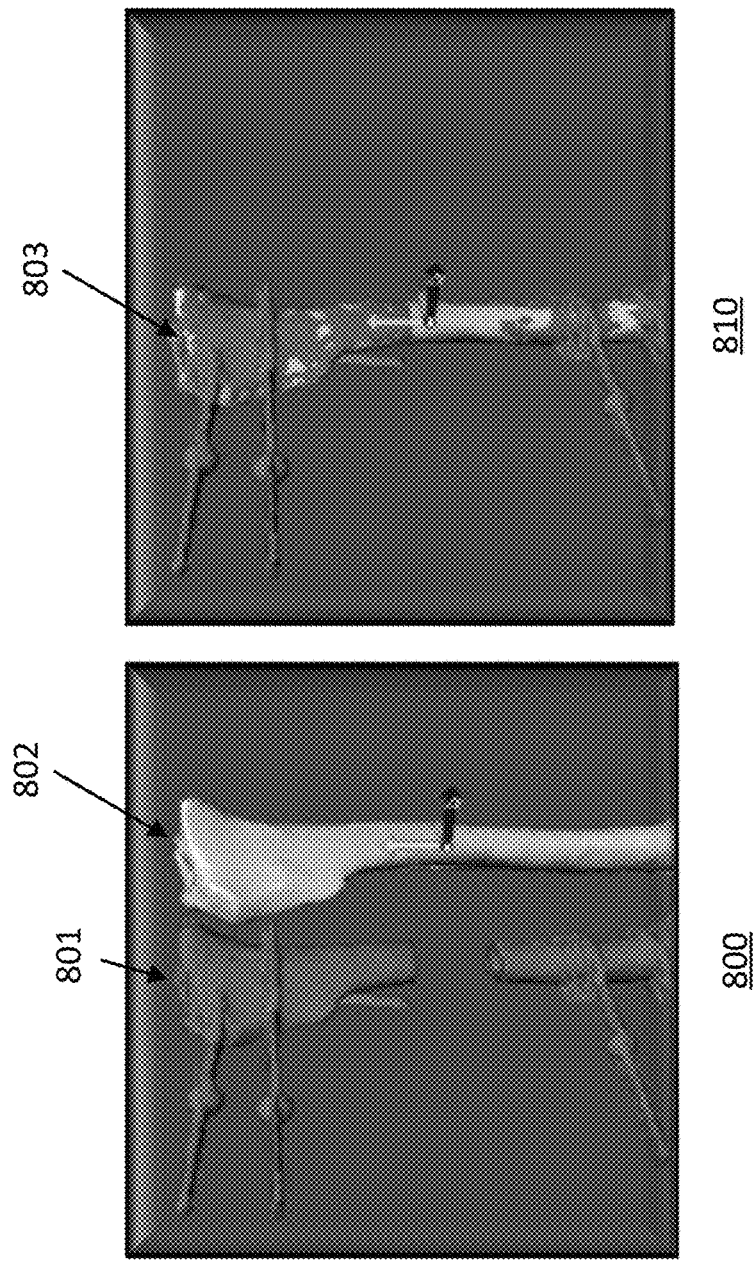
FIG. 8 provides two images of a model of a bone segment undergoing a virtual reduction using a bone comparison method in accordance with some of the approaches disclosed herein.
Figure 9:
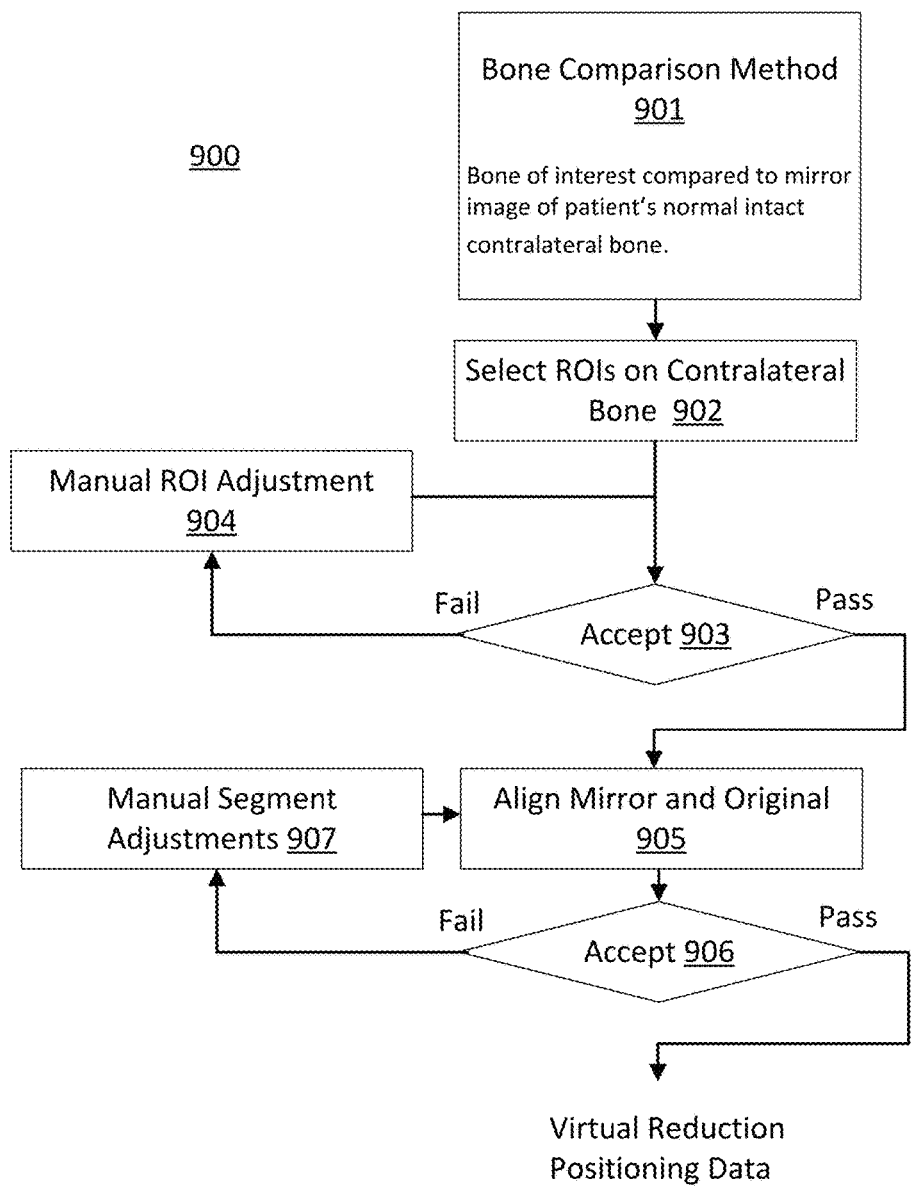
FIG. 9 provides a flow charts each for a set of methods for conducting a virtual reduction and generating an optimal bone alignment and virtual reduction positioning data using a bone comparison method in accordance with some of the approaches disclosed herein.

The software realigns the bone fragments or bone length, angulation or torsion as desired based on an algorithm and anatomic landmarks that uses imaging from contralateral bones, bone templates and a database of normal values as necessary. Using this, the software creates a three dimensional object around the selected object/area that fits precisely (i.e. accounts for volume of printing material, print accuracy, and can alter print density/mesh density within desired selected regions). Additionally, the software detects and filters out noise and artifact inherent with image acquisition with post processing algorithms that allow for optimal image presentation (surface smoothing etc.). The software can display a three-dimensional virtual model of osseous structures, and any present interaction elements, in a manner that can be manipulated by the user to precisely translate the virtual osseous-interaction element constructs into desired positions. FIGS. 7-9 present three different techniques for doing this, respectively predicated on a bone comparison method, a shattered column method, and a normal value method. A fourth technique involves a manual virtual reduction in which the bone segments are moved and aligned by a user with the assistance of software alignment guides.

FIG. 7 provides a flow chart 700 for a shattered column method and a flow chart 710 for a normal value method. In the shattered column method 701 software reconstructs the various fragments to form a column of bone by rejoining the segments. The software effectively positions a column in the virtual model and attempts to fill the column with the bone segments while minimizing gaps in the column. Flow chart 700 also include a step 702 of determining if the virtual reduction is acceptable by a user's review. If the virtual reduction fails this review, manual adjustments can be made in a step 703 and the shattered column solver can be run again after the adjustments. In the normal value method 711, a solver uses population normal values for the bone in question such as joint angulation and bone length to guide the reconstruction. This approach does not require an intact contralateral bone. The approaches use specific angles and lengths based on bone landmarks to adjust the two major segments that contain the articular surfaces such that the bone length and joint angles are the same as the normal values that are generated from a population of similar patients. Like the shattered column method, the normal value method can be augmented with a check on the virtual reduction 712, and the optional manual adjustment of the bone segments in a step 713. However, this check can involve either a user's manual review, or an automated check to see if the joint angles and limb lengths match the selected normal values and an automated request for manual adjustments if the check fails.

FIGS. 8 and 9 can be used to describe an example of the bone comparison method for conducting the virtual reduction. Flow chart 900 includes a bone comparison method 901 in which a diaphyseal fracture can be deleted in the model and articular fragments are manipulated to achieve desired bone length and joint angles as measured on a mirror image of an intact contralateral bone. This process is illustrated in FIG. 8 by image 800 in which the bone in question 801 has been aligned with the fracture deleted, and a mirror image of the intact contralateral bone 802 is positioned to be aligned with the bone in question 801. As seen in image 810, the two modeled constructs can be overlain 803 to check if the modeled alignment of the two segments of the bone in question are properly aligned.

The bone comparison method requires the intact bone to be analyzed and brought into the model in order to facilitate the comparison. As such, flow chart 900 includes a step 902 of selecting ROIs on the normal mirrored contralateral bone in order to obtain data for creating a three-dimensional model of the contralateral bone. Step 902 can be augmented with a manual check step 903 to assure that enough ROIs are available to properly generate the three-dimensional model, and a manual adjustment of the ROIs 904 in case that check fails. Flow chart 900 also includes a step 905 in which software aligns the major segments from the bone of interest to find a best fit position using the mirrored intact contralateral bone as a template. This process can also be done manually by a user that is able to manipulate the two elements using a user interface. Flow chart 900 also includes a step 906 in which the reduction can be evaluated by a user and a step 907 in which manual adjustments to the virtual reduction can be conducted.

Figure 10:
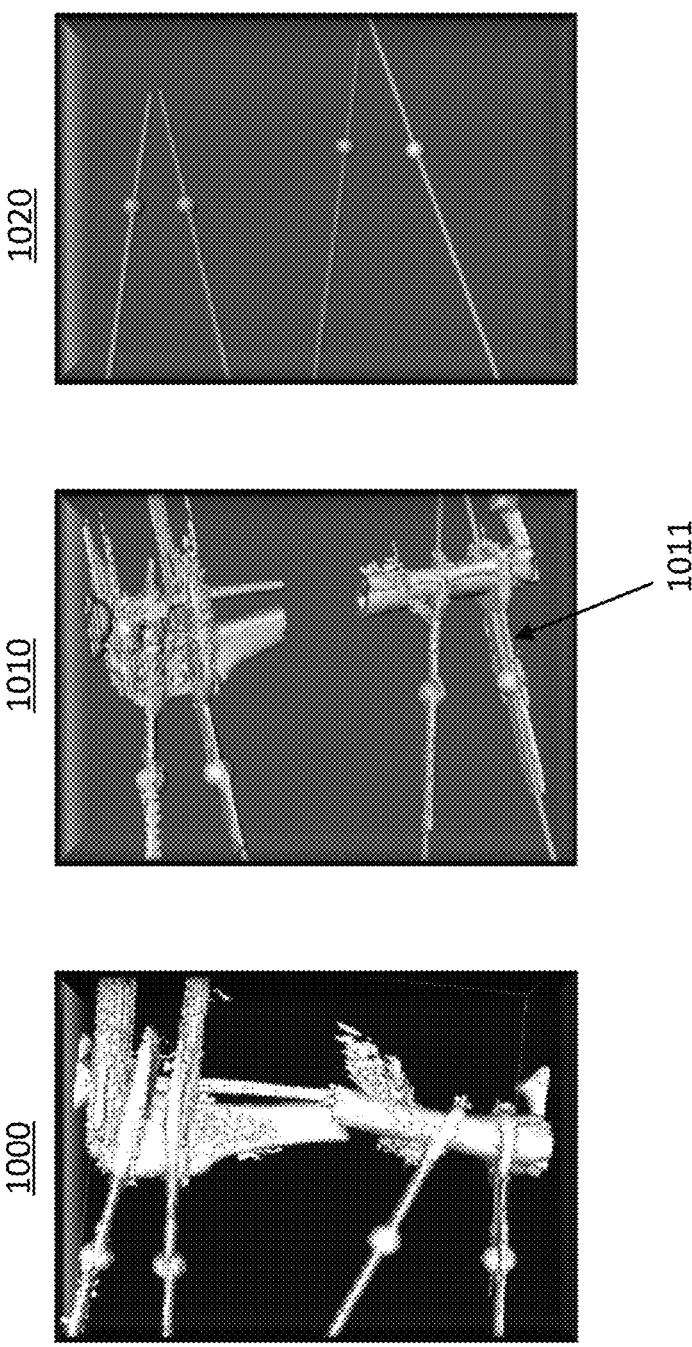
FIG. 10 provides two images of a three-dimensional model of two bone segments with attached interaction elements and some associated distortion being used for a virtual reduction in accordance with some of the approaches disclosed herein.

FIG. 10 provides three images generated from a model of bone segments and attached interaction elements. First image 1000 shows the bone segments misaligned, second image 1010 shows the same bone segments after virtual alignment using any of the processes described above, and third image 1020 shows the model after the bone segments have been removed and the interaction elements have been replaced with virtual models thereof. Once the bone segments have been virtually aligned as in image 1010, the interaction elements in the model can be replaced with accurate virtual models of the interaction pins such as interaction element templates. The virtual models can be created from preexisting knowledge regarding the interaction elements. As a result, the virtual model can be a more accurate representation of the interaction element than the modeled version of the interaction element as derived from an analysis of the interaction element itself. This can be done using several approaches as described below. This technique can provide certain advantages in that imaging artifacts, such as those caused by flare magnification from metal interaction elements 1011, can obfuscate the true position of the interaction pin relative to the bone segment. The virtual models of the interaction pins can incorporate specific alterations (positive or negative mechanical stops, screw threading ability or morse taper) to match the actual interaction pins used when the model was first obtained, or to match modifications to the interaction pins that will be added after the original imaging, but prior to the actual physical reduction of the bone segments.

The replacement of the interaction pins in the model can be conducted using software via a best-fit method using one or a combination of volume, line, point clouds or manual fit. In volume detection, replacement best fit spheres can be placed within the "column" of the interaction element and the line connecting the centers of the volumes can be used to establish the direction of the imaged interaction element. In the line method, two tapered points of an interaction element can be identified in the model and a line connection between the two points can be connected to establish the center and direction of the imaged interaction element. In the point cloud method, slices from the model can be used and a best fit ellipse around the interaction element can be best fit to each slice. A best fit line can then be drawn from the center points of each of the ellipses to determine the direction of the imaged interaction element. In the manual fit method, the operator can manually match the template to best fit the imaged implant with a virtual model to replace it. In approaches in which the interaction elements include a mechanical stop, the mechanical stop can be identified by finding the center of the volume of the stop and replacing it with a virtual model of the stop along the previously established line of the imaged interaction element.

As described with reference to FIG. 11, the imaged interaction elements can be replaced with virtual models after the model has been used to conduct a virtual alignment. The imaged interaction elements could instead be replaced at any time, including immediately after the bone segment and attached interaction elements are analyzed. However, certain benefits accrue to approach in which additional model elements are not introduced that need to be independently manipulated through the course of the virtual reduction because doing so could spike the processing time required to conduct the virtual reduction.

Once the bone segments have undergone a virtual reduction, data can be harvested from the model in order to design a customized jig to implement the actual reduction. This data can include a determined spatial arrangement of bone segments and an associated spatial arrangement of the interaction elements. This collection of data can be referred to as the virtual reduction positioning data. Once the desired configuration of the bone is achieved, interaction element landmarks can be used in combination with the virtual reduction positioning data to generate the customized jig and any of its component parts. A data package can be generated containing the information required to print the components and application guidelines. In approaches in which the virtual reduction is practiced by another party such as a skilled worker operating in a remote facility, the data package can be delivered to a user located in close proximity to the patient over a network in order to use the data package to rapidly manufacture the custom jig.

Figure 11:
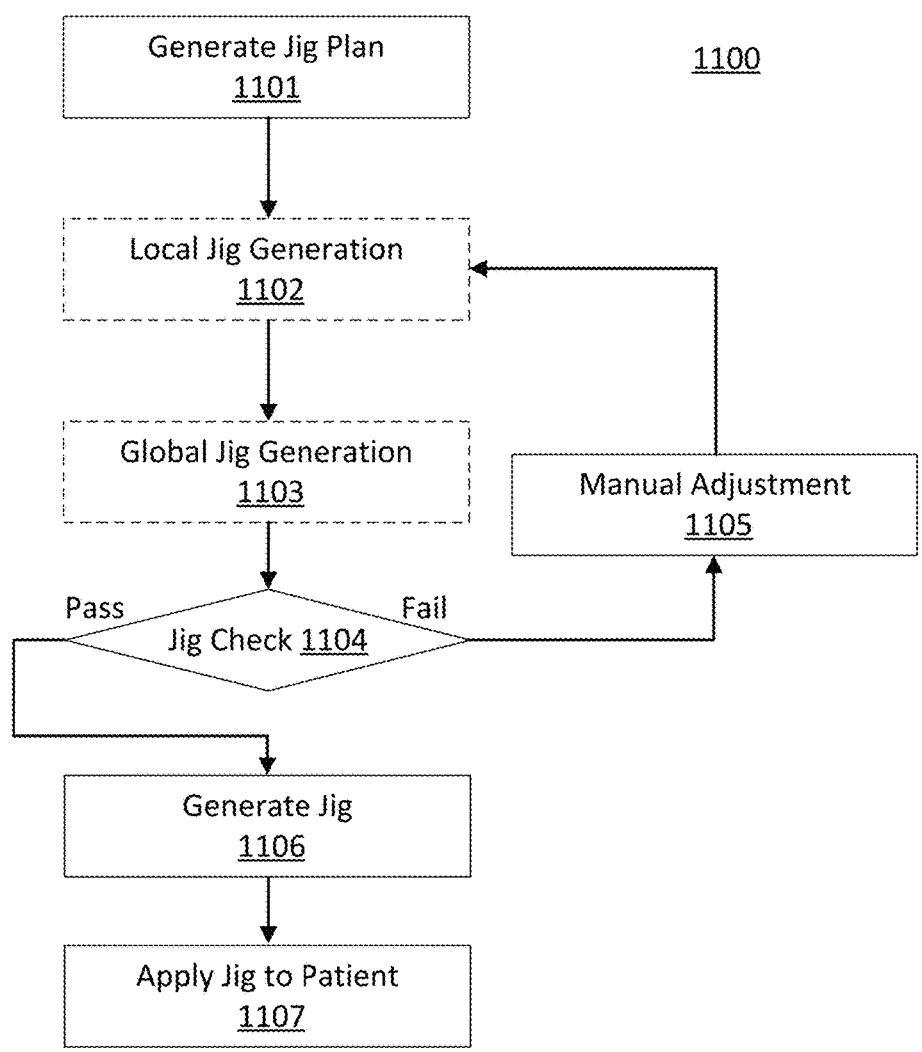
FIG. 11 provides a flow chart for a set of methods for generating a customized jig and applying it to a patient in accordance with some of the approaches disclosed herein.

FIG. 11 provides a flow chart 1100 for a set of methods for generating a customized jig and applying it to a patient. The process can utilize a model of the patient's bone segments, and optional interaction elements, as generated according to the procedures described above. The process can also utilize a data package derived from the virtual reduction procedures described above. In a first step 1101, a customized jig plan is generated. This can be conducted using the data package and initial data selected by a user when first identifying which kind of customized jig and interaction elements should be utilized for a given patient. As mentioned, multiple kinds of interaction elements and customized jigs can be generated including multi-component jigs, percutaneous interaction elements, noninvasive interaction elements, lateral jigs, annular jigs, and other variations disclosed herein. The generation of the plan can also involve modification to the interaction elements if the data package identified deficiencies with the current interaction elements. These modifications can likewise be implemented using components physically generated using the same hardware used to generate the customized jig.

The remainder of flow chart 1100 is directed to the specific case of a multi-component customized jig configured to guide surgically attached interaction elements during the reduction process. The multi-component jig includes at least one local jig component and a global jig component. As such, flow chart 1100 continues with a step 1102 of local jig generation and a step 1103 of global jig generation. Both steps are drawn using dotted lines to indicate the fact that each is optional. This is because the customization offered by a multi-component jig can be afforded by customizable local jig components with prefabricated global jigs, customizable global jig components with prefabricated local jigs, both customizable global and local jigs, or prefabricated but adjustable global and local jigs. Furthermore, single-component customized jigs can be generated using similar procedures by simply condensing steps 1102 and 1103 into a single step of generating the jig design in memory for that single-component.

Three-dimensional printing can be minimized by the use of prefabricated components which are assembled and/or configured in response to the modeling, for example, to represent customizable lengths and angles of parts interaction. As such, all of step 1103 is optional because the global jig could be a prefabricated component of the customized jig that can be reused. In these approaches, the overall jig is customized in the sense that customized local jigs are generated on a per patient or per procedure basis. A prefabricated global jig could have arms that receive local jigs. The global jig could have arms that receive the local jigs. The arms could be manipulated to adjust the effective length, rotation, and angulation afforded by the global jig. The specific length, rotation and angulation values necessary for a desired alignment could be determined virtually as part of the data package produced by the virtual alignment process described above. In these approaches, the prefabricated global jig would be applied to the local jigs virtually in order to solve for these adjustment values. In the same manner, all of step 1104 is optional because the local jigs could be prefabricated components of the customized jig that can be reused. In these approaches, the overall jig is customized in the sense that global jigs are generated on a per patient or per procedure basis. A prefabricated local jig could function to provide pilot hole drill guides as well as an interaction element placement guide, while a customized global jig determined the relative position, rotation, and angulation values required for a given reduction. Again, the customized values could be determined virtually and be part of the data package mentioned above. Finally, the global jig and/or local jigs could be adjustable pre-fabricated components that were adjustable to implement a desired reduction, and the parameters associated with these adjustments could be solved for using the virtual reduction and be part of the data package described above.

Steps 1102 and 1103 can be conducted by a three-dimensional printer either fully generating the elements or by printing a portion of the overall components that will be used in the reduction procedure. In one embodiment, the jig plan generator and printing software are built into the same system as the analysis (e.g., imaging) and modeling software referenced above, but it can also optionally instead be instantiated in a standalone or networked system. For example, the jig plan generator and printing software can be embodied in computer system and three-dimensional printer operated in-situ to produce the jig in near-real-time (i.e., in minutes). In one embodiment, the software communicates with and directly controls a three-dimensional printer for printing in a variety of printable materials as selected by a user, for example, to both directly design and then control in-situ printing of custom interaction elements and a custom jig. Additionally, in one embodiment, the software can communicate with virtual reality equipment, allowing for direct three-dimensional interaction via this technology for all steps of the described processes. Optionally, the software can be embodied in the form of one or more servers or other computer systems that interact with peripherals, such as the three-dimensional printer, imaging devices, and mass storage and network components as required. In one implementation, these devices can be operatively connected via local or wide area network (i.e., via "LAN" or "WAN").

Flow chart 1100 can continue with a step 1104 in which a user is allowed to review a three-dimensional model of the customized jig before it is fabricated along with the option to manually adjust the customized jig in a step 1105 if that check fails. The flow chart then continues with a step 1106 in which the customized jig is physically generated. The customized jig can be created via three-dimensional printing in situ, under control of the software. The customized jig can also be created in the sense that adjustable prefabricated components can be adjusted to a desired physical configuration as solved for using the virtual reduction and further processing of the bone segments in software. The customized jig can be configured to attach to the interaction elements and/or bone segments and be used to retain the structure in the shape modeled by software. Customized replacement interaction elements, or modifications to the interaction elements, can also be optionally created (e.g., three-dimensional printing in situ) based on any the identified areas of deficiency discovered during the virtual reduction, jig plan generation, or any manual review thereof. Finally, the custom jig and/or modified interaction elements can then be added via a second surgical procedure, with additional software modeling applied to ensure proper fit and maintenance of desired state during the recovery procedure.

Figure 12:
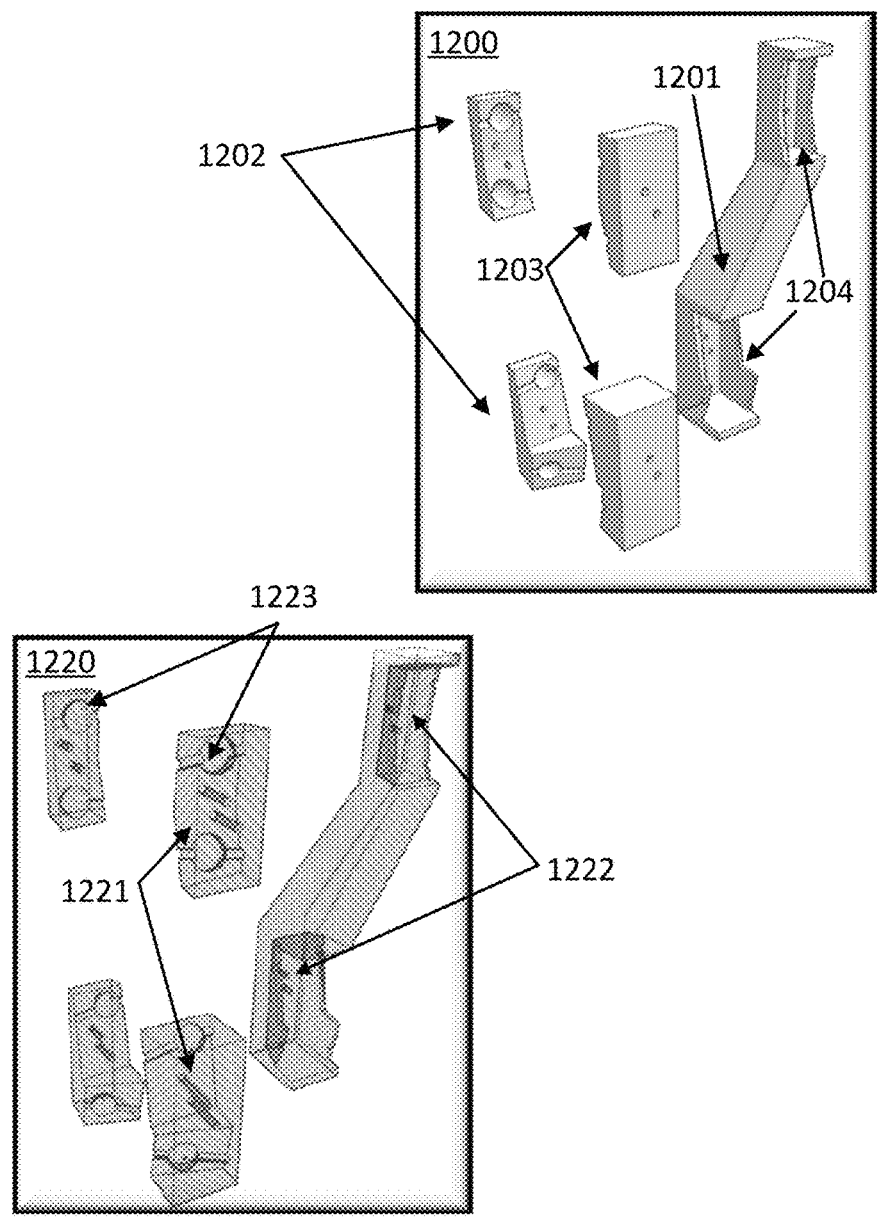
FIG. 12 provides two views of a customized jig having a global jig component and at least one local jig component in accordance with some of the approaches disclosed herein.
Figure 13:
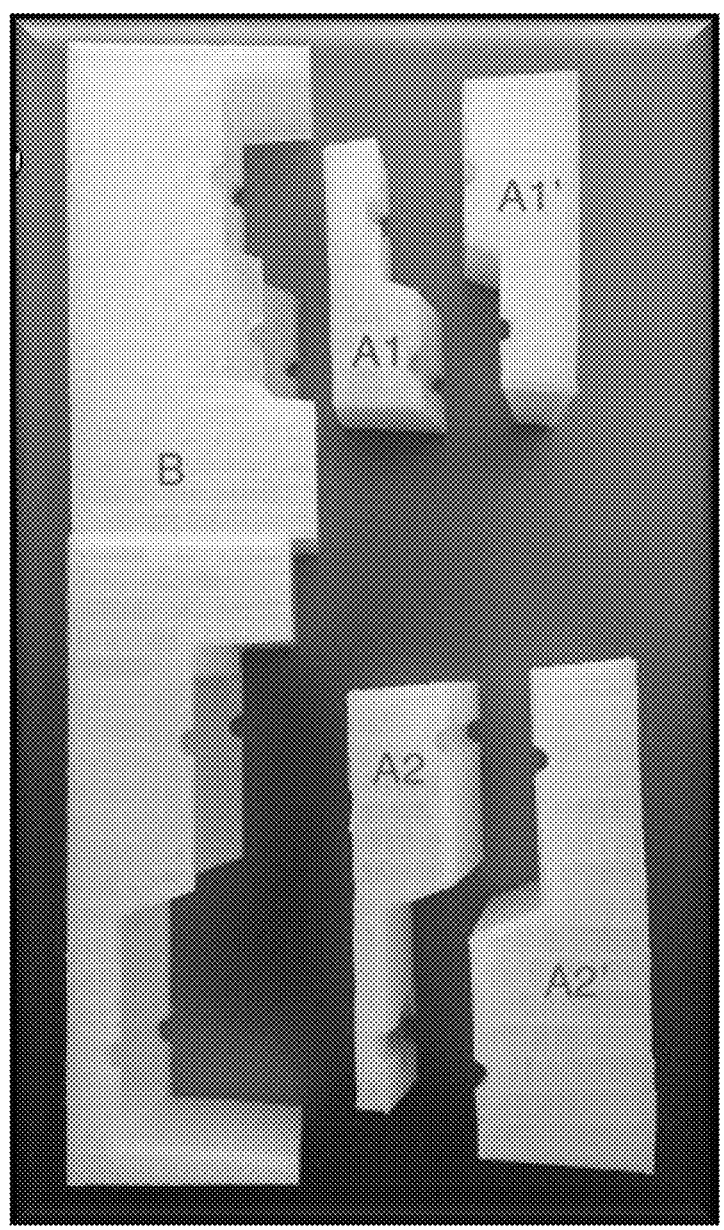
FIG. 13 provides a photograph of a three-dimensional printed customized jig in accordance with some of the approaches disclosed herein.

An example of a customized jig that can be generated in accordance with the disclosures herein is provided with reference to FIGS. 12-14. FIG. 12 includes two exploded views 1200 and 1210 of a customized jig where the individual components are translucent in view 1210 to show the interior details of the customized jig. The customized jig is a multicomponent lateral jig including a global jig element 1201 and two local jig elements. The local jig elements each individually include two sub-elements 1202 and 1203. The global jig element includes two recesses 1222 that can be used in the reduction process. Specifically, the local jig element components 1202 and 1203 can first be attached to a pair of interaction elements, one attached to each bone segment in the reduction. The combined local jig elements can then be engaged with recesses 1222, one for each recess. Local jig element components 1203 can include screw holes 1221 that can be used to engage local jig element components 1203 with their counterpart local jig element components 1202, and to further engage the combined local jig elements with the global jig. As illustrated, both the counterpart local jig element components 1202 and the recesses 1222 can include screw holes for this purpose. As seen in view 1220, local jig element components 1221 and 1220 can also provide an impression into which the interaction elements can be inserted and secured. As illustrated, the interaction elements could be interaction pins with mechanical stops configured to align with mechanical stop outlines 1223 on the local jig element components, 1203 and 1202, to keep the interaction pins in place through the reduction procedure. The interaction elements can be guided through a reduction path while the local jig elements are engaged with the recesses, and a reduction stop can be reached with the local jig elements are fully engaged with the recesses. At the point at which the local jig elements are fully engaged, the bone segments will have been translated to their optimal alignment. However, similar procedures can be conducted FIG. 13 provides a photograph of a specific implementation of a customized jig that is in accordance with the customized jigs disclosed with reference to FIG. 12. In this case, the local jig element components of a first local jig are labeled A1 and A1', and the local jig element components of a second local jig are labeled A2 and A2'. Furthermore, the global jig is labeled B. In FIG. 13, the local jig elements can be referred to as minor interaction implant clamps (MIIC) and the global jig can be referred to as a major alignment construct (MAC). The MIIC of FIG. 13 is a two-part clamp that encompasses the interaction implants at the level of mechanical stops and is divided along the plane of the implants such that the two pieces can be sandwiched and compressed onto the implants. One MIIC is needed for each manipulated bone segment. The MAC is a connecting structure that incorporates the MIICs. The MAC functions to hold the MIICs and their associated bone segments in the desired location as modeled in the software. This is accomplished by manipulating the MIICs so that they fit within the corresponding negative MIIC space of the MAC. The MIIC-MAC interface is designed as a 5-sided tapered interface such that the insertion tip of the MIIC is smaller than the base allowing easy insertion of the MIICs into the MAC with final precise reduction being achieved as the MIICs are compressed into the MAC.

The MICC-MAC assembly of FIG. 12 is configured to interact with a specific type of interaction element that transmit force from the jig to the bone and consist of three sections The first section inserts/attaches into/to the bone in a semi-permanent manner. The second section has a unique shape that allows for tight attachment of the implant with the custom jig. The interaction elements are made from a variety of materials that are best chosen for the application desired and include metallic, plastic and composite components. The MAC can be a premade connecting bar section, (consisting of modular components of metallic or composite construction that attach to the interaction elements or custom three-dimensionally printed section in such a manner as to reduce the fracture or attain the desired position of the bone). This premade connecting bar has the function of reducing the amount of printing that is required but does not preclude the use of a printed connecting bar.

FIG. 14 provides four images of the recess of a customized reduction jig that is in accordance with the MICC-MAC assembly described with reference to FIG. 13. Images 1400 and 1410 provides a view of the lower recess on a MAC assembly B. Image 1410 provides a view of that recess with a first element of the local jig A engaged with the lower recess. Image 1420 includes the addition of the first element of the local jig A engaged into the recess. Image 1420 also illustrates interaction pins 1422 and pilot hole screws 1423. The pilot hole screws 1422 can extent through two 2.5 mm pilot holes. Image 1420 shows how the interaction pins 1421 can be supported by the first element of the local jig A, and how the pilot hole screws extend through the first element of the local jig A. One of those pilot hole screws extends entirely through the first element of the local jig A into a screw hole 1401 in the lower recess on MAC assembly B. The other pilot hole screw extend only through a second element of the local jig B and terminates in a screw hole 1411 on the first element of the local jig A. The global jig, in this case MAC assembly B is modeled so that it completely encompasses the first element of the local jig A. However, it does not encompass the second element of the local jig A' along the long axis of the interaction elements. When the interaction element volumes are subtracted it can be seen that the first element of the local jig A of is enclosed on five surfaces by MAC assembly B, but no one component encircles an interaction element. The system can also have a series of protective sleeves and drill guides to reduce soft tissue injury and improve the accuracy of the system. Additional templates that provide accurate interaction implant positioning can also be part of the system. When both sets of the local jig elements are fully engaged with the MAC assembly, the interaction elements will have been guided to the optimal alignment found in the virtual reduction process that was used to generate the customized jig.

Figure 15:
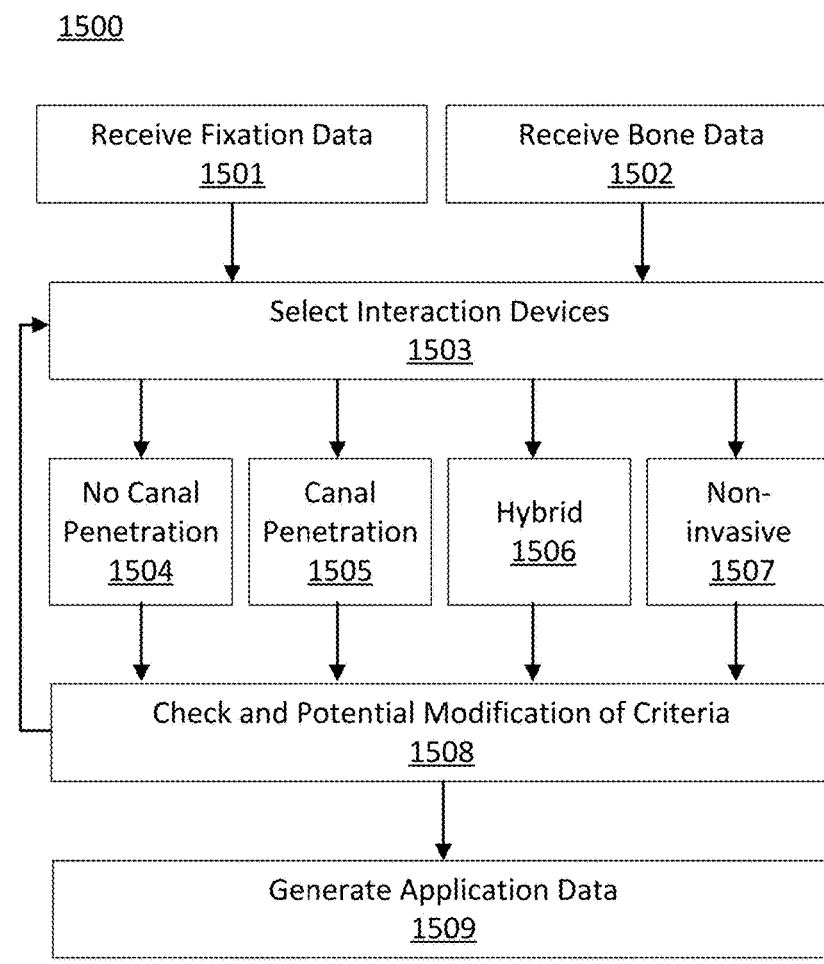
FIG. 15 provides a flow chart for a set of methods for selecting a type of interaction device and generating application data in accordance with approaches disclosed herein.

FIG. 15 provides a flow chart 1500 for a set of methods for selecting the appropriate fixation device and components selected and applied to the bone segment. In steps 1501 and 1502 desired definitive fixation and preliminary bone data, describing bone configuration/morphology, can be received from a surgeon. Based on this information, the most appropriate interaction elements can be chosen in a step 1503. The interaction elements can be percutaneous interaction elements that do not penetrate the medullary canal 1504, those that do penetrate the canal 1505, or a hybrid combination of those kinds of elements 1506. The interaction elements can also be a non-invasive fixation device such as a hard-shell sleeve 1507. The selected fixation device can then be assessed for acceptability, and if the device is unacceptable then modifications to the criteria can be selected in a step 1508. In the case of an unacceptable selection, a new device can be selected in another execution of step 1503. The output of flow chart 1500 can be the application data generated in step 1509 in which a specific interaction element and the manner in which those application elements will be applied is output. This information can be used to guide the virtual reduction and customized jig generation, and interaction element generation steps mentioned above.

Figure 16:
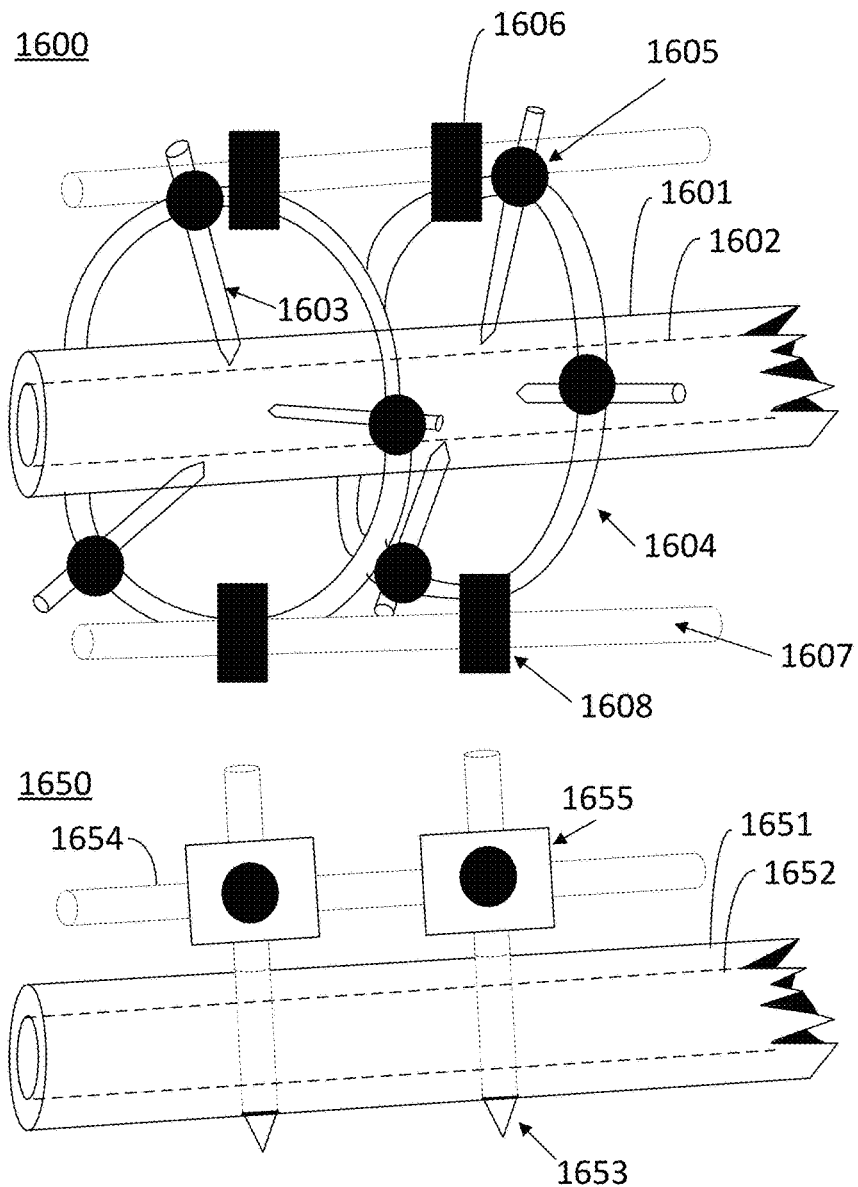
FIG. 16 provides two diagrams: one of an interaction element and includes external stabilizing rings and percutaneous pins that do not pierce the medullary canal, and one of interaction pins that do pierce the medullary canal, both of which are in accordance with approaches disclosed herein.

FIG. 16 provides two examples of alternative interaction elements that can be used in accordance with some of the systems and methods disclosed herein. In both diagrams, the surrounding tissue has been removed to more clearly illustrate the interaction elements. Diagram 1600 shows a single bone segment 1601 having medullary cavity 1602. The illustrated interaction elements include pins 1603 that do not pierce the medullary cavity 1602. Pins 1603 are connected to rings 1604 that surround the bone segment and are connected to the pins via pin-ring connections 1605. Rings 1604 are themselves connected to interaction pins 1607 via another type of pin-ring assembly 1608. The interaction pins 1607 can then be connected to a customized jig in order to guide the bone segment into alignment in accordance with some of the approaches disclosed herein. Diagram 1650 includes an additional approach in which a bone segment 1651 with a medullary cavity 1652 is attached to pins 1653 that do pierce the medullary cavity 1652. In this approach, the pins are connected directly to an interaction pin 1654 via pin-pin assemblies 1655. The interaction pin 1654 can then be connected to a customized jig in order to guide the bone segment into alignment in accordance with some of the approaches disclosed herein.

Figure 17:
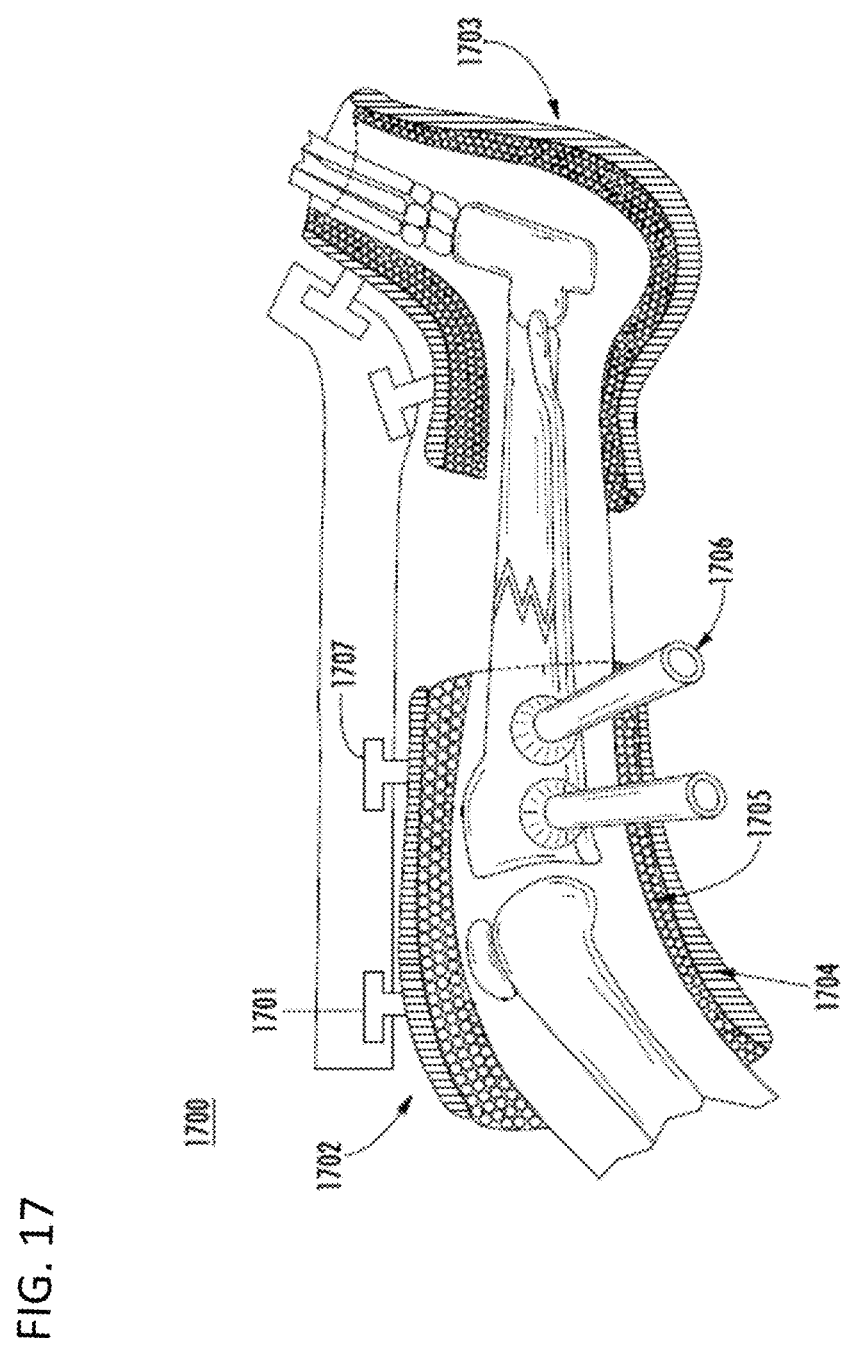
FIG. 17 provides a diagram of a set of interaction elements and includes an external hard-shell sleeve by which the interaction elements are indirectly attached to the bone segments in accordance with approaches disclosed herein.

FIG. 17 provides an example of an alternative interaction element that can be used in accordance with some of the systems and methods disclosed herein. Diagram 1700 shows two bone segments indirectly attached to interaction elements 1701 via a hard-shell sleeve 1702 applied to a first bone segment and a second hard shell sleeve 1703 applied to a second bone segment. The hard-shell sleeve comprises a rigid external shell 1704. The sleeve can also include a layer of compressive material 1705 to be placed in proximity to the patient's skin. The sleeve can also include pin application guides 1706 in order to allow for the optional addition of percutaneous pins to assist in the reduction or to provide additional support for other purposes. Once the sleeve has been applied to both bone segments, the interaction elements 1701 can be engaged with a customized jig 1707. As interaction elements 1701 are engaged with jig 1707, the bone segments can be guided into alignment in accordance with some of the approaches disclosed herein An example usage of specific embodiments disclosed above includes the use of the described methods and systems to reduce a fracture in patient's bone. In this example, a patient sustains trauma to the tibia and has a mid-shaft fracture composed of 10 fragments with both the distal and proximal articular surfaces intact. Interaction elements in the form of interaction implants could be surgically attached are placed percutaneously into the proximal and distal segments that contain the articular surfaces. Advanced imaging (CT or MRI) could then be used to scan the bone with the implants in place. The data could then be used to generate a three-dimensional model of the fragments with the implants. The fragments could then be virtually manipulated to restore the bone length and alignment to acceptable or desired values. Following this, a reduction construct is modeled around the interaction implants and printed using a three-dimensional printer and based on the outcome of the virtual reduction. Then, the printed construct could be attached to the interaction implants, and the bone fragments/implants translated and maintained in real space to the corresponding predetermined position in virtual space determined during the virtual reduction. Depending on the desired outcome, the reduction construct may be a customized jig and may be used as a temporary jig for a permanent method of fixation or may be used as the definitive fixation method.

Another example usage of specific embodiments disclosed above includes the use of the described methods and systems to correct an angular limb deformity in a patient's bone. In this example, a patient has an angular limb deformity that requires correction. Certain methods disclosed above allow for precise correction to desired limb angle values. The limb in question can be assessed non-invasively (CT, MRI or radiographically) and the centers of rotation of angulation (CORA's) can be determined. Based on this, interaction elements, in the form of implants, can be placed into the major bone fragments avoiding proposed osteotomy sites. The limb can then be imaged (CT or MRI) and reconstructed. CORA based virtual osteotomies can then be made in the model and the bone segments aligned such that the angular limb deformity is resolved. Two virtual models can be created. The first model attaches to the implants to precisely guide the osteotomies and is then removed. The second model works as described in the previous example to reduce and stabilize the fragments to the predetermined position in virtual space.

The performance of an approach in accordance with certain embodiments described herein has been presented by both inventors separately at two national surgery conventions—the ACVS Surgery Summit 2017 and the Veterinary Orthopedic Society Conference 2018. The manuscript of those presentations was included in the provisional applications to which this application claims priority.

Variations of the disclosed system can be used for various other purposes besides bone aligned. For example, variations can also be used for bone stabilization where the interaction elements can be used for external skeletal fixation (ESF). Variations could also be used for healing elements where the system is used as a precision targeting device for injection of osteogenetive, osteoinductive, osteoconductive, osteopromotive substances. The system could also be used as a targeting system for transcutaneous therapies (e.g., cold-laser therapy, extracorporeal shockwave therapy etc.). The system could also be used for manipulation of bone segments in a timed process to allow for gradual movement of the bone segments (e.g., for limb lengthening procedures or correction of angular limb deformities). The system could include motors or robotic arms used to manipulate the interaction elements for this purpose, and for movement of the interaction elements generally. The system could be modified to utilize augmented reality where an intraoperative vision system displayed the spatial positioning of the corresponding bone segments. The augmented reality system could generate this information based on the position of exposed interaction elements and knowledge of the relationship of those elements to the underlying bone segments as provided by a model of the bone segments and attached interaction elements. The system could also be modified to include the use of robotic arms used to manipulate the interaction elements instead of a jig system. The movement of the robotic arms could be programmed using the same information used to generate the jig. The system could also be modified to include the attachment of monitors to the interaction elements to monitor stress/strain and other mechanical variables on the interaction elements. Such an approach could allow a user to monitor healing when using an ESF as well as providing other utility.

While the specification has been described in detail with respect to specific embodiments of the invention, it will be appreciated that those skilled in the art, upon attaining an understanding of the foregoing, may readily conceive of alterations to, variations of, and equivalents to these embodiments. Any of the method steps discussed above can be conducted by a processor operating with a computer-readable non-transitory medium storing instructions for those method steps. The computer-readable medium may be memory within a personal user device or a network accessible memory. Although examples in the disclosure where generally directed to repairing fractures, the same approaches could be utilized to other boney malalignments via the use of a custom jig and/or custom implants. These and other modifications and variations to the present invention may be practiced by those skilled in the art, without departing from the scope of the present invention, which is more particularly set forth in the appended claims.

What is claimed is:

1. A reduction method for aligning a first bone segment and a second bone segment comprising:
   surgically attaching: (i) a first interaction implant to the first bone segment; and (ii) a second interaction implant to the second bone segment;
   imaging the first and second bone segments to create a model;
   processing the model to find an optimal bone alignment;
   generating, based on the optimal bone alignment and with a three-dimensional printer, a custom jig, wherein the custom jig includes a global jig element, a first local jig element, and a second local jig element;
   attaching the first local jig element to the first interaction implant;
   attaching the second local jig element to the second interaction implants; and
   engaging, after attaching the custom jig to the first and second interaction implants, the first and second local jig elements with the global jig element;
   wherein the first and second bone segments are translated as the first and second local jig elements are engaged with the global jig element; and
   wherein the first bone segment and second bone segment are properly aligned in the optimal bone alignment.

2. The method of claim 1, wherein:
   the first and second bone segments are aligned according to the optimal bone alignment when the first and second local jig elements are fully engaged with the global jig element.

3. The method of claim 1, wherein:
   the global jig element is not customized and is available prior to the commencement of the method; and
   the first and second local jig elements are customized.

4. The method from claim 1, wherein:
   the imaging of the first and second bone segments step is conducted after the surgical attaching of the first and second interaction implants to the first and second bone segments step; and
   the model includes the first and second interaction implants.

5. The method from claim 4, further comprising:
   editing the model by replacing: (i) the first interaction implant with a first virtual interaction implant; and (ii) the second interaction implant with a second virtual interaction implant;
   wherein the generating of the custom jig based on the optimal bone alignment step includes using: (i) a first position of the first virtual interaction implant; and (ii) a second position of the second virtual interaction implant; and
   wherein first and second bone segments are in the optimal bone alignment when the first and second virtual interaction implants are in the first and second positions.

6. The method from claim 5, wherein:
   the editing of the model step is conducted after the processing of the model to find the optimal bone alignment step.

7. The method from claim 1, wherein:
   the first interaction pin penetrates a medullary cavity of the first bone segment;
   the second interaction pin penetrates a medullary cavity of the second bone segment; and
   the custom jig is a lateral jig.

8. The method from claim 7, wherein:
   the global jig element has a first recess and a second recess;
   the engaging of the first and second local jig elements with the global jig element includes: (i) guiding the first local jig element into the first recess; and (ii) guiding the second local jig element into the second recess; and
   the first and second bone segments are aligned according to the optimal bone alignment when the first and second local jig elements are fully engaged with the global jig element.

9. The method from 1, further comprising:
   surgically attaching a first set of interaction pins to the first bone segment, wherein surgically attaching the first set of interaction pins includes surgically attaching the first interaction pin to the first bone segment, and wherein the first interaction pin is in the first set of interaction pins;
   surgically attaching a second set of interaction pins to the first bone segment, wherein surgically attaching the first set of interaction pins includes surgically attaching the first interaction pin to the first bone segment, and wherein the first interaction pin is in the first set of interaction pins; that are penetrates a medullary cavity of the first bone segment;
   wherein none of the pins in the first and second sets of interaction pins penetrate the medullary cavity;
   wherein the first set of interaction pins are connected by a first ring that surrounds the first bone segment when the first set of interaction pins are attached to the first bone segment;
   wherein the second set of interaction pins are connected by a second ring that surrounds the second bone segment when the second set of interaction pins are attached to the second bone segment; and
   wherein the attaching of the custom jig to the first and second interaction implants consists of: (i) attaching the first interaction implant to the first local jig element via the first ring; and (ii) attaching the second interaction implant to the second local jig element via the second ring.

10. A reduction method for aligning a first bone segment and a second bone segment comprising:

surgically attaching: (i) a first interaction implant to the first bone segment; and (ii) a second interaction implant to the second bone segment;

imaging the first and second bone segments to create a model;

processing the model to find an optimal bone alignment;

generating, based on the optimal bone alignment and with a three-dimensional printer, a custom jig, wherein the custom jig includes a global jig element and at least one local jig element;

attaching the custom jig to the first and second interaction implants; and engaging, after attaching the custom jig to the first and second interaction implants, the at least one local jig element with the global jig element;

wherein at least one of the first and second bone segments are translated as the at least one local jig element is engaged with the global jig element; and wherein the first bone segment and second bone segment are properly aligned in the optimal bone alignment.

11. The method of claim 10, wherein:
the first and second bone segments are aligned according to the optimal bone alignment when the at least one local jig element is fully engaged with the global jig element.

12. The method of claim 10, wherein:
the global jig element is not customized and is available prior to the commencement of the method; and
the at least one local jig element is customized.

13. The method from claim 10, wherein:
the imaging of the first and second bone segments step is conducted after the surgical attaching of the first and second interaction implants to the first and second bone segments step; and
the model includes the first and second interaction implants.

14. The method from claim 13, further comprising:
editing the model by replacing: (i) the first interaction implant with a first virtual interaction implant; and (ii) the second interaction implant with a second virtual interaction implant;
wherein the generating of the custom jig based on the optimal bone alignment step includes using: (i) a first position of the first virtual interaction implant; and (ii) a second position of the second virtual interaction implant; and
wherein first and second bone segments are in the optimal bone alignment when the first and second virtual interaction implants are in the first and second positions.

15. The method from claim 14, wherein:
the editing of the model step is conducted after the processing of the model to find the optimal bone alignment step.

16. The method from claim 10, wherein:
the first interaction pin penetrates a medullary cavity of the first bone segment;
the second interaction pin penetrates a medullary cavity of the second bone segment; and
the custom jig is a lateral jig.

17. The method from claim 16, wherein:
the global jig element has at least one recess;
the engaging of the at least one local jig element with the global jig element includes guiding the at least one local jig element into the at least one recess; and the first and second bone segments are aligned according to the optimal bone alignment when the at least one local jig element is fully engaged with the at least one recess.

18. The method from 17, wherein:
the at least one local jig element includes a first local jig element and a second local jig element;
the at least one recess includes a first recess and a second recess;
the custom jig includes the first local jig element, the second local jig element, and the global jig element; and
the first and second bone segments are aligned according to the optimal bone alignment when: (i) the first local jig element is fully engaged with the first recess; and (ii) the second local jig element is fully engaged with the second recess.

19. The method from claim 10, wherein:
the at least one local jig element includes a first local jig element and a second local jig element;
the custom jig includes the first local jig element, the second local jig element, and the global jig element;
the attaching of the custom jig to the first and second interaction implants step consists of: (i) attaching the first interaction implant to the first local jig element; and (ii) attaching the second interaction implant to the second local jig element; and
the first and second bone segments are both translated as the first and second local jig elements are engaged with the global jig element.

20. The method from 19, further comprising:
surgically attaching a first set of interaction pins to the first bone segment, wherein surgically attaching the first set of interaction pins includes surgically attaching the first interaction pin to the first bone segment, and wherein the first interaction pin is in the first set of interaction pins;
surgically attaching a second set of interaction pins to the first bone segment, wherein surgically attaching the first set of interaction pins includes surgically attaching the first interaction pin to the first bone segment, and wherein the first interaction pin is in the first set of interaction pins; that are penetrates a medullary cavity of the first bone segment;
wherein none of the pins in the first and second sets of interaction pins penetrate the medullary cavity;
wherein the first set of interaction pins are connected by a first ring that surrounds the first bone segment when the first set of interaction pins are attached to the first bone segment;
wherein the second set of interaction pins are connected by a second ring that surrounds the second bone segment when the second set of interaction pins are attached to the second bone segment; and
wherein the attaching of the custom jig to the first and second interaction implants consists of: (i) attaching the first interaction implant to the first local jig element via the first ring; and (ii) attaching the second interaction implant to the second local jig element via the second ring.

21. A reduction method for aligning a first bone segment and a second bone segment comprising:
attaching: (i) a first interaction element to the first bone segment; and (ii) a second interaction element to the second bone segment;
imaging the first and second bone segments to create a model;

processing the model to find an optimal bone alignment, wherein the first bone segment and second bone segment are aligned in the optimal bone alignment;

generating, with a three-dimensional printer, a custom jig; and guiding the first and second interaction elements with the custom jig;

wherein the first and second bone segments are aligned according to the optimal bone alignment when the first and second interaction elements are guided to a reduction stop on the custom jig.

22. The method of claim 21, wherein:

the first interaction element is noninvasively attached to the first bone segment via a first rigid shell; and the second interaction element is noninvasively attached to the first bone segment via a second rigid shell.

23. The method from claim 21, wherein:

the imaging of the first and second bone segments step is conducted after the attaching of the first and second interaction elements step; and the model includes the first and second interaction elements.

24. The method from claim 23, wherein:

the generating of the custom jig based on the optimal bone alignment step includes using: (i) a first position of the interaction element; and (ii) a second position of the second interaction element; and first and second bone segments are in the optimal bone alignment when the first and second interaction elements are in the first and second positions.

* * * * *

UNITED STATES PATENT AND TRADEMARK OFFICE
CERTIFICATE OF CORRECTION

PATENT NO. : 10,426,552 B2
APPLICATION NO. : 15/937842
DATED : October 1, 2019
INVENTOR(S) : John Adam Davies et al.

Page 1 of 1

It is certified that error appears in the above-identified patent and that said Letters Patent is hereby corrected as shown below:

In the Claims

Column 18, Claim 9, Line 36, please insert --claim-- after "The method from...".
Column 18, Claim 9, Line 48, please delete "are" after "interaction pins; that...".
Column 20, Claim 18, Line 5, please insert --claim-- after "The method from...".
Column 20, Claim 20, Line 31, please insert --claim-- after "The method from...".
Column 20, Claim 20, Line 43, please delete "are" after "interaction pins; that...".

Signed and Sealed this
Twenty-first Day of January, 2020

Andrei Iancu
*Director of the United States Patent and Trademark Office*